US012507967B2

(12) United States Patent
Dangashiya et al.

(10) Patent No.: US 12,507,967 B2
(45) Date of Patent: Dec. 30, 2025

(54) FLOATING CRADLE PATIENT TABLE WITH MULTI-MODALITY IMAGING CAPABILITY

(71) Applicant: GE Precision Healthcare LLC, Waukesha, WI (US)

(72) Inventors: Dhaval Pravinbhai Dangashiya, Ahmedabad (IN); Ramachandra Gururaja Rao, Bangalore (IN); Vishwanath Nayak, Bangalore (IN); Goutam Maji, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 223 days.

(21) Appl. No.: 18/454,971

(22) Filed: Aug. 24, 2023

(65) Prior Publication Data

US 2025/0064414 A1 Feb. 27, 2025

(51) Int. Cl.

| | |
|---|---|
| ***A61B 6/04*** | (2006.01) |
| ***A61B 6/00*** | (2024.01) |
| ***A61B 6/03*** | (2006.01) |

(52) U.S. Cl.

CPC .......... *A61B 6/0407* (2013.01); *A61B 6/0487* (2020.08); *A61B 6/032* (2013.01); *A61B 6/4441* (2013.01); *A61G 2210/50* (2013.01)

(58) Field of Classification Search

CPC ....... A61B 6/032; A61B 6/035; A61B 6/0487; A61B 6/0407; A61B 6/4441; A61B 6/0428; A61G 2210/50

See application file for complete search history.

(56) References Cited

U.S. PATENT DOCUMENTS

| | | | | |
|---|---|---|---|---|
| 4,475,072 | A * | 10/1984 | Schwehr .............. | A61B 6/0487 318/54 |
| 6,382,393 | B2 * | 5/2002 | Itoh ........................ | B65G 47/54 198/370.09 |
| 6,508,586 | B2 | 1/2003 | Oota | |
| 6,769,145 | B1 * | 8/2004 | Pfeffer ................. | A61B 6/0442 5/601 |
| 7,467,004 | B2 | 12/2008 | Calderon et al. | |
| 10,702,223 | B2 | 7/2020 | Stoutenburgh et al. | |

(Continued)

FOREIGN PATENT DOCUMENTS

| | | |
|---|---|---|
| CN | 108882904 | 11/2018 |
| JP | 3728418 B2 | 12/2005 |

OTHER PUBLICATIONS

EP application 24193298.7 filed Aug. 7, 2024—extended Search Report issued Jan. 8, 2025; 8 pages.
JP3728418 English Translation; 16 pages.

*Primary Examiner* — David J Makiya
*Assistant Examiner* — Miya Downing
(74) *Attorney, Agent, or Firm* — Fletcher Yoder, P.C.

(57) ABSTRACT

A patient table for a computed tomography (CT) imaging system is provided. The patient table includes a base. The patient table also includes a floating cradle configured to support a subject to be imaged and to move bi-directionally relative to the base. The patient table further includes a fixed structure coupled to the base. The patient table further includes a plurality of rollers mounted to the fixed structure. The plurality of rollers is configured both to guide and to support the floating cradle. The floating cradle is configured to guide itself when extend beyond the fixed structure.

17 Claims, 21 Drawing Sheets

(56) References Cited

U.S. PATENT DOCUMENTS

| | | | |
|---|---|---|---|
| 10,799,143 B2 | 10/2020 | Menon et al. | |
| 2017/0020466 A1 | 1/2017 | Moulin | |
| 2023/0329651 A1* | 10/2023 | Boxall | A61B 6/102 |

* cited by examiner

FLOATING CRADLE PATIENT TABLE WITH MULTI-MODALITY IMAGING CAPABILITY

BACKGROUND

The subject matter disclosed herein relates to imaging systems and, more particularly, to a floating cradle patient table with multi-modality imaging capability.

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the reflection of acoustic waves, to acquire data and to construct images or otherwise represent the observed internal features of the patient.

For example, in computed tomography (CT) and other X-ray based imaging technologies, X-ray radiation spans a subject of interest, such as a human patient, and a portion of the radiation impacts a detector where the image data is collected. In digital X-ray systems a photodetector produces signals representative of the amount or intensity of radiation impacting discrete pixel regions of a detector surface. The signals may then be processed to generate an image that may be displayed for review. In CT imaging systems, a detector array, including a series of detector elements, produces similar signals through various positions as a gantry is displaced around a patient.

A patient is moved into and out a bore of a gantry of the CT scanner via a patient table. A typical CT patient table typically includes long stationary beam structures (e.g., extruded beam structures) with linear motion guide rails mounted on to guide a patient supporting cradle during its movement into and out of the gantry. This structure of the patient table imposes a constraint on the room size layout for CT system installation. In addition, maneuvering of a gantry cover of the gantry presents a challenge to a field engineer in performing service due to the longer beam structures of the CT patient table. Overall, the typical CT table structure is bulky which makes packaging, transportation, rigging, and installation complex. Further, the longer beam structures of the CT patient table that does not enable or support the utilization of some radiology, therapy, or procedures (e.g., interventional radiography, image-guided therapy, fluoroscopy, angiography, etc.) in harmony with other imaging devices (e.g., fixed-radiology, fluoroscopy, fixed C-arm, mobile C-arm, etc.). In particular, a patient table of these other imaging devices cannot be used for CT-based radiology, therapy, or procedures due to the scan range movement of the cradle of the CT patient table for the CT scan. A floor mounted linear motion guide rails would be needed for the CT gantry and a larger scan would be needed to enable this. Further, to enable this, the CT patient table structure would become so complex and bulky (and expensive) and the table length significantly increased (e.g., by 80 percent) that it would result in increased table cradle deflection which would present challenge with regard to image quality.

SUMMARY

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In one embodiment, a patient table for a computed tomography (CT) imaging system is provided. The patient table includes a base. The patient table also includes a floating cradle configured to support a subject to be imaged and to move bi-directionally relative to the base. The patient table further includes a fixed structure coupled to the base. The patient table even further includes a plurality of rollers mounted to the fixed structure. The plurality of rollers is configured both to guide and to support the floating cradle. The floating cradle is configured to guide itself when extended beyond the fixed structure.

In another embodiment, a computed tomography (CT) imaging system is provided. The CT imaging system includes a gantry coupled to imaging components configured to acquire imaging data of a subject. The CT imaging system also includes a patient table. The patient table includes a base. The patient table also includes a floating cradle configured to support a subject to be imaged and to move bi-directionally relative to the base. The patient table further includes a fixed structure coupled to the base. The patient table further includes a plurality of rollers mounted to the fixed structure. The plurality of rollers is configured both to guide and to support the floating cradle. The floating cradle is configured to guide itself when extended beyond the fixed structure.

In a further embodiment, a patient table for an imaging system is provided. The patient table includes a base. The patient table also includes a floating cradle configured to support a subject to be imaged and to move bi-directionally relative to the base. The patient table further includes a fixed structure coupled to the base. The fixed structure includes a pair of beams flanking a portion of the floating cradle. The pair of beams extend in a direction parallel to a longitudinal axis of the floating cradle. A first length of the floating cradle along the longitudinal axis is greater than a respective length of each beam of the pair of beam in the direction.

BRIEF DESCRIPTION OF THE DRAWINGS

These and other features, aspects, and advantages of the disclosed subject matter will become better understood when the following detailed description is read with reference to the accompanying drawings in which like characters represent like parts throughout the drawings, wherein.

DETAILED DESCRIPTION

Figure 1:
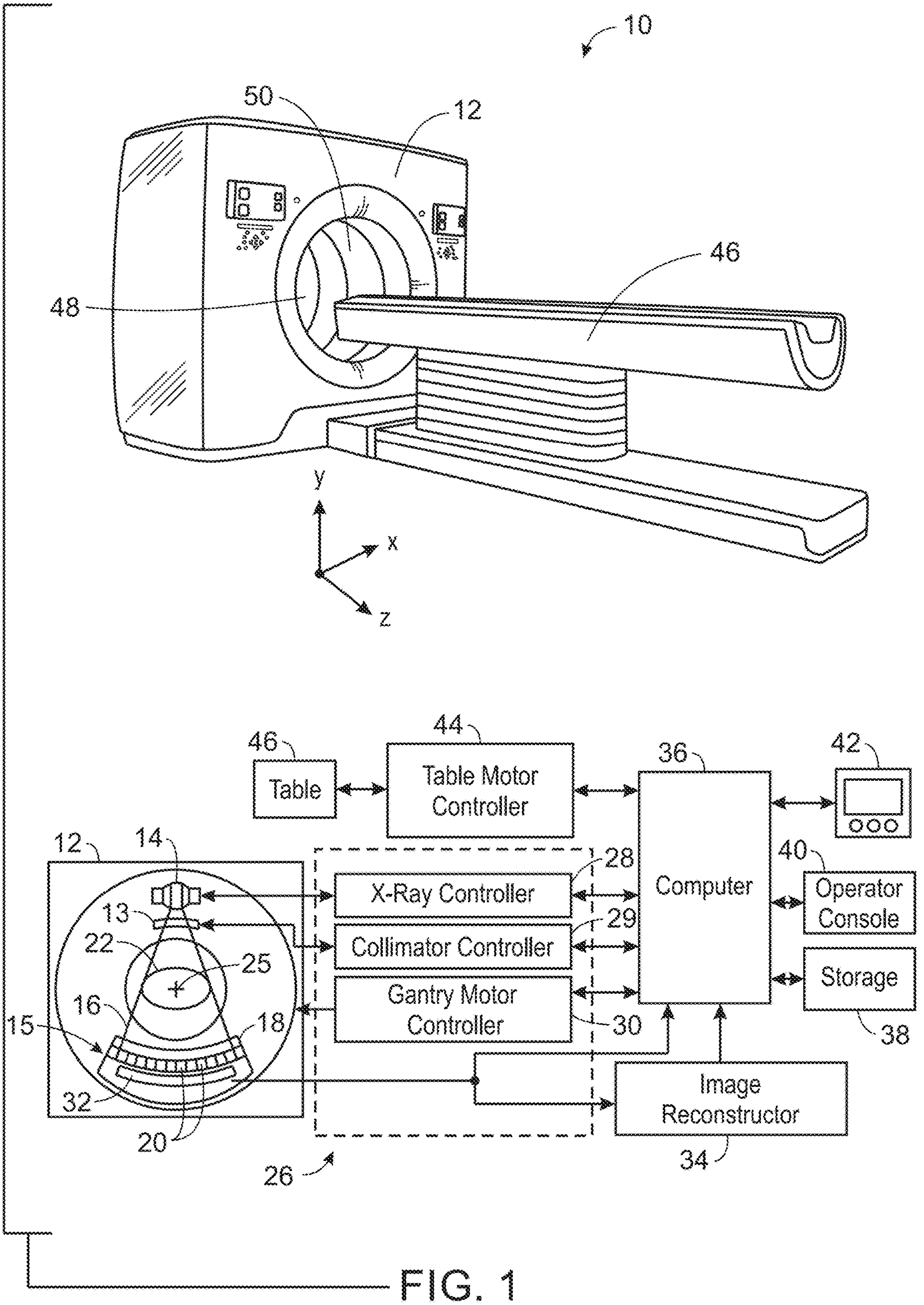
FIG. 1 is a combined pictorial view and block diagram of a computed tomography (CT) imaging system as discussed herein.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion are provided in the context of medical imaging, it should be appreciated that the disclosed techniques are not limited to such medical contexts. Indeed, the provision of examples and explanations in such a medical context is only to facilitate explanation by providing instances of real-world implementations and applications. However, the disclosed techniques may also be utilized in other contexts, such as image reconstruction for non-destructive inspection of manufactured parts or goods (i.e., quality control or quality review applications), and/or the non-invasive inspection of packages, boxes, luggage, and so forth (i.e., security or screening applications). In general, the disclosed techniques may be useful in any imaging or screening context or image processing or photography field where a set or type of acquired data undergoes a reconstruction process to generate an image or volume.

The present disclosure provides embodiments for a patient table of medical imaging systems (e.g., a computed tomography (CT) imaging system) that includes a floating cradle. The patient table includes a base. In certain embodiments, the base is fixed. In certain embodiments, the base is configured to move bi-directionally in a vertical direction (e.g., relative to the floor). The patient table also includes a floating cradle configured to support a subject to be imaged and to move bi-directionally relative to the base (which provides useful scan range availability on both sides of the patient table). The patient table further includes a fixed structure coupled to the base. The patient table even further includes a plurality of rollers (e.g., guide rollers) mounted to the fixed structure. The plurality of rollers is configured both to guide and to support the floating cradle. The floating cradle is configured to guide itself when extended beyond the fixed structure.

In certain embodiments, the fixed structure includes a pair of beams (e.g., extruded beams) flanking a portion of the floating cradle, wherein the pair of beams extend in a direction parallel to a longitudinal axis of the floating cradle. A first length of the floating cradle along the longitudinal axis is greater than a respective length of each beam of the pair of beams in the direction. The fixed structure includes a first side and a second side opposite the first side, wherein the first side is configured to face a gantry of the CT imaging system. The floating cradle is configured to enable a scan of the subject on the floating cradle on at least one of the first side and the second side with an imaging system both separate from and different from the CT imaging system (e.g., C-arm imaging). This enables multiple imaging devices to be utilized in a single room.

In certain embodiments, the plurality of rollers includes a first set of rollers disposed above the floating cradle and a second set of rollers disposed below the floating cradle. In certain embodiments, the first set of rollers is configured to retain the floating cradle on the fixed structure. In certain embodiments, the at least one roller of the second set of rollers is configured to support the floating cradle and at least one roller of the second set of rollers is configured to drive movement of the floating cradle bi-directionally relative to the base. In certain embodiments, the second set of rollers includes a friction drive roller configured to drive the movement of the floating cradle bi-directionally relative to the base and a pair of rollers flanking the friction drive roller and configured to support the floating cradle. In certain embodiments, the second set of rollers includes a roller configured to support the floating cradle and a pair of friction drive rollers flanking the roller and configured to drive the movement of the floating cradle bi-directionally relative to the base.

In certain embodiments, the plurality of rollers includes a third set of rollers disposed on a first side and second side of the floating cradle, wherein both the first side and the second side extend between a top surface and a bottom surface of the floating cradle. In certain embodiments, at least one roller of the third set of rollers is configured to guide movement of the floating cradle bi-directionally relative to the base. In certain embodiments, at least one roller of the third set of rollers is configured to retain the floating cradle on the fixed structure. In certain embodiments, at least one roller of the third set of rollers is configured to drive movement of the floating cradle bi-directionally relative to the base. In certain embodiments, the third set of rollers includes a first roller disposed on the first side of the floating cradle and a second roller disposed on the second side of the floating cradle, and both the first roller and the second roller are configured to drive the movement of the floating cradle bi-directionally relative to the base.

In certain embodiments, the patient table includes a cable retractor (e.g., adjustable cable retractor). the cable retractor includes a first end structure coupled to the fixed structure, a second end structure coupled to a longitudinal end of the floating cradle, and a cord extending between the first end structure and the second end structure. The cable retractor is configured to keep the longitudinal end of the floating cradle from extending beyond a fixed distance from the fixed structure. The cable retractor is also configured to be adjusted to change or to set the fixed distance. In certain embodiments, the patient table includes a sensor (e.g., anti-collision sensor) coupled to a longitudinal end of the floating cradle. The sensor is configured to sense an object and to send a signal to stop movement of the floating cradle to avoid collision with the object.

The disclosed embodiments provide a patient table having a floating cradle that reduces the room size requirement for the CT scanner. The disclosed embodiments also enable making transportation, handling, and installation easier. For example, the symmetric configuration of the fixed structure and the floating cradle enables mirrored installation of the table with respect to the gantry (i.e., either longitudinal end can be installed adjacent to the gantry). The disclosed embodiments further include making serviceability easier due to the ease of gantry cover maneuvering which results in less downtime for the CT imaging system. The disclosed embodiments provide an enhanced platform for a patient table to be utilized with multiple imaging modalities (e.g., due to the useful scan range availability on both sides of the patient table). The disclosed embodiments yet further include reduce cost due to the elimination of using long beam structures. The disclosed embodiments even further provide a low-cost solution for a multi-modality interventional/imaging environment within a common scan room. The disclosed embodiments yet further provide a faster scan flow in this multi-modality interventional/imaging environment.

With the preceding in mind and referring to FIG. 1, a computed tomography (CT) imaging system 10 is shown, by way of example. The CT imaging system 10 includes a gantry 12. The gantry 12 has an X-ray source 14 that projects a beam of X-rays 16 toward a detector assembly 15 on the opposite side of the gantry 12. The X-ray source 14 projects the beam of X-rays 16 through a pre-patient collimator assembly 13 that determines the size and shape of the beam of X-rays 16. The detector assembly 15 includes a collimator assembly 18 (a post-patient collimator assembly), a plurality of detector modules 20 (e.g., detector elements or sensors), and data acquisition systems (DAS) 32. The plurality of detector modules 20 detect the projected X-rays that pass through a subject or object 22 being imaged, and DAS 32 converts the data into digital signals for subsequent processing. Each detector module 20 in a conventional system produces an analog electrical signal that represents the intensity of an incident X-ray beam and hence the attenuated beam as it passes through the subject or object 22. During a scan to acquire X-ray projection data, gantry 12 and the components mounted thereon rotate about a center of rotation 25 (e.g., isocenter) so as to collect attenuation data from a plurality of view angles relative to the imaged volume.

Rotation of gantry 12 and the operation of X-ray source 14 are governed by a control system 26 of CT imaging system 10. Control system 26 includes an X-ray controller 28 that provides power and timing signals to an X-ray source 14, a collimator controller 29 that controls a length and a width of an aperture of the pre-patient collimator 13 (and, thus, the size and shape of the beam of X-rays 16), and a gantry motor controller 30 that controls the rotational speed and position of gantry 12. An image reconstructor 34 receives sampled and digitized X-ray data from DAS 32 and performs high-speed image reconstruction. The reconstructed image is applied as an input to a computer 36, which stores the image in a storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, collimator controller 29, and gantry motor controller 30. In addition, computer 36 operates a table motor controller 44, which controls a motorized table 46 (e.g., patient table) to position subject 22 and gantry 12. Particularly, table 46 moves portions of subject 22 through a gantry opening or bore 48.

Figure 2:
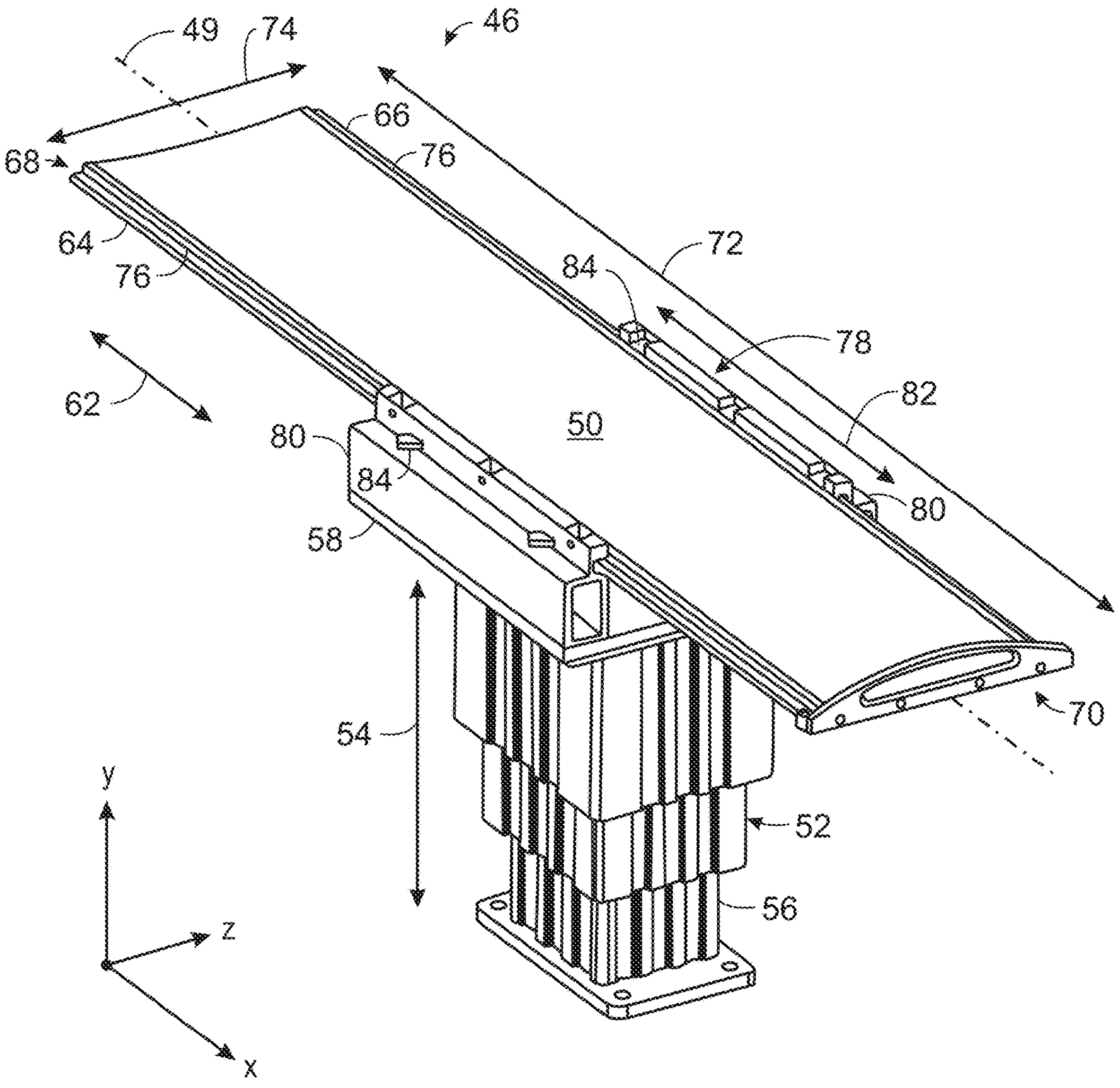
FIG. 2 is a perspective view of the patient table of the CT imaging system in FIG. 1 (e.g., having a base configured to move vertically), in accordance with aspects of the present disclosure.
Figure 3:
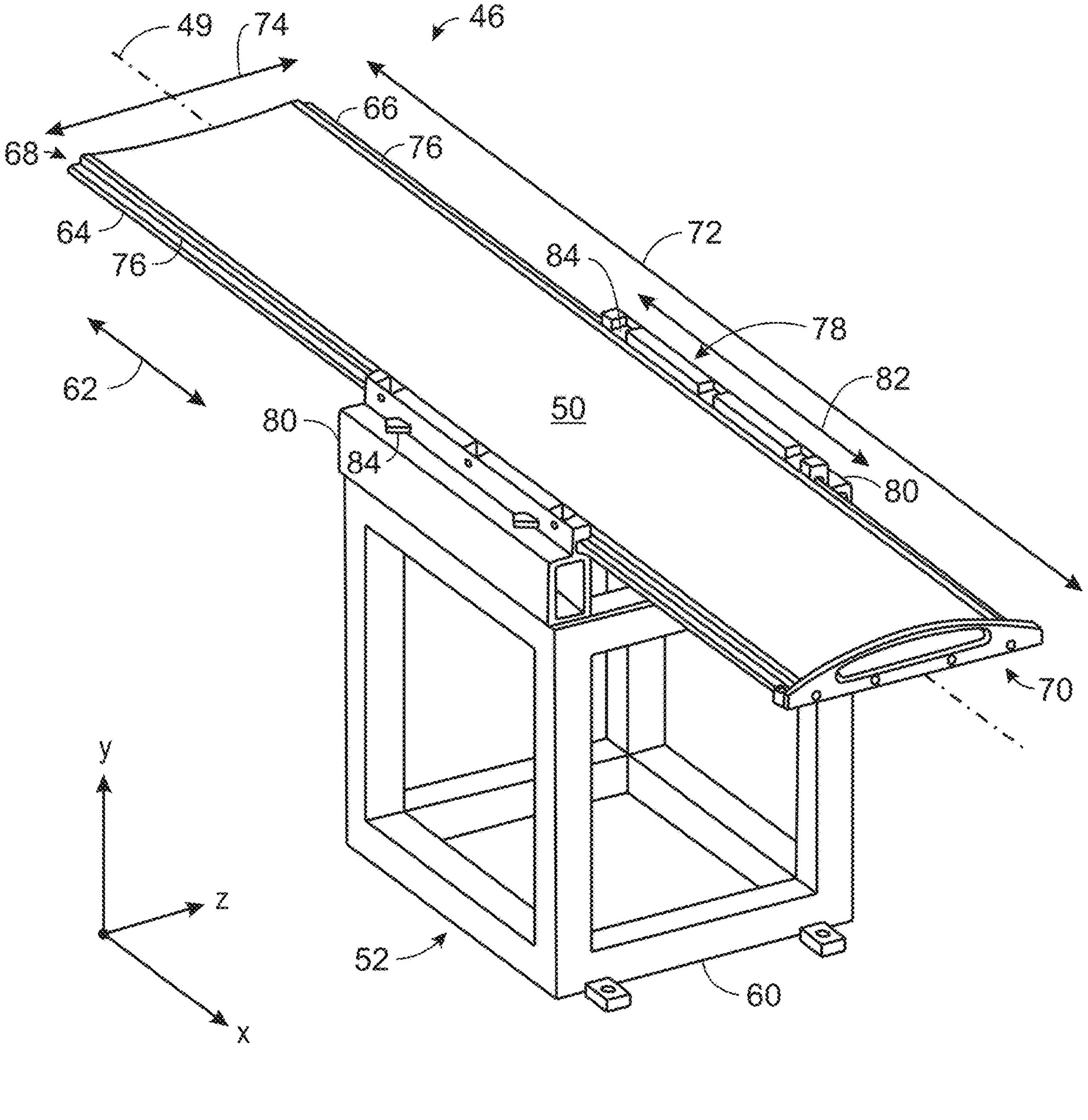
FIG. 3 is a perspective view of the patient table of the CT imaging system in FIG. 1 (e.g., having a fixed base), in accordance with aspects of the present disclosure.
Figure 4:
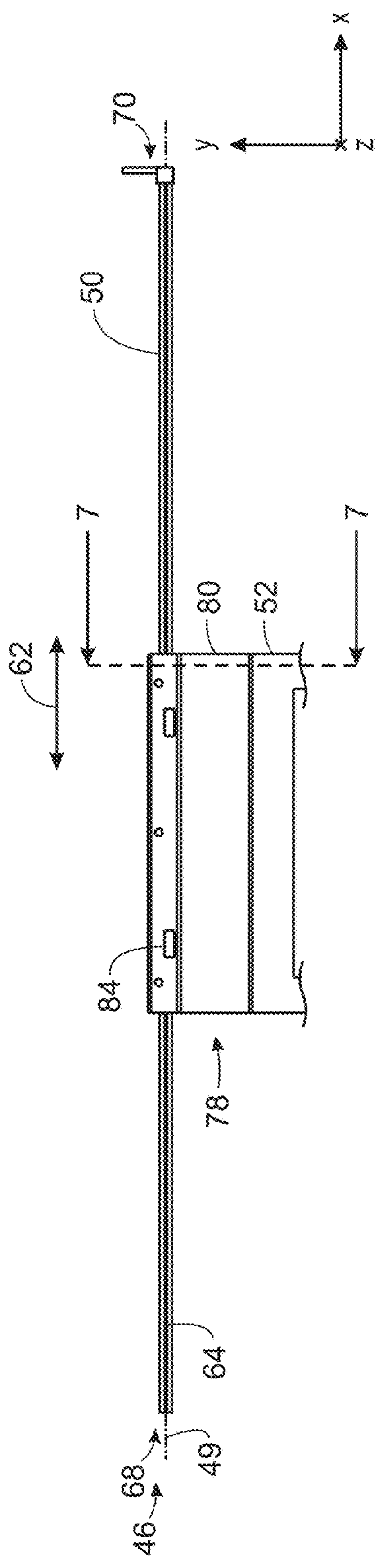
FIG. 4 is a side view of the patient table of the CT imaging system in FIG. 3, in accordance with aspects of the present disclosure.
Figure 5:
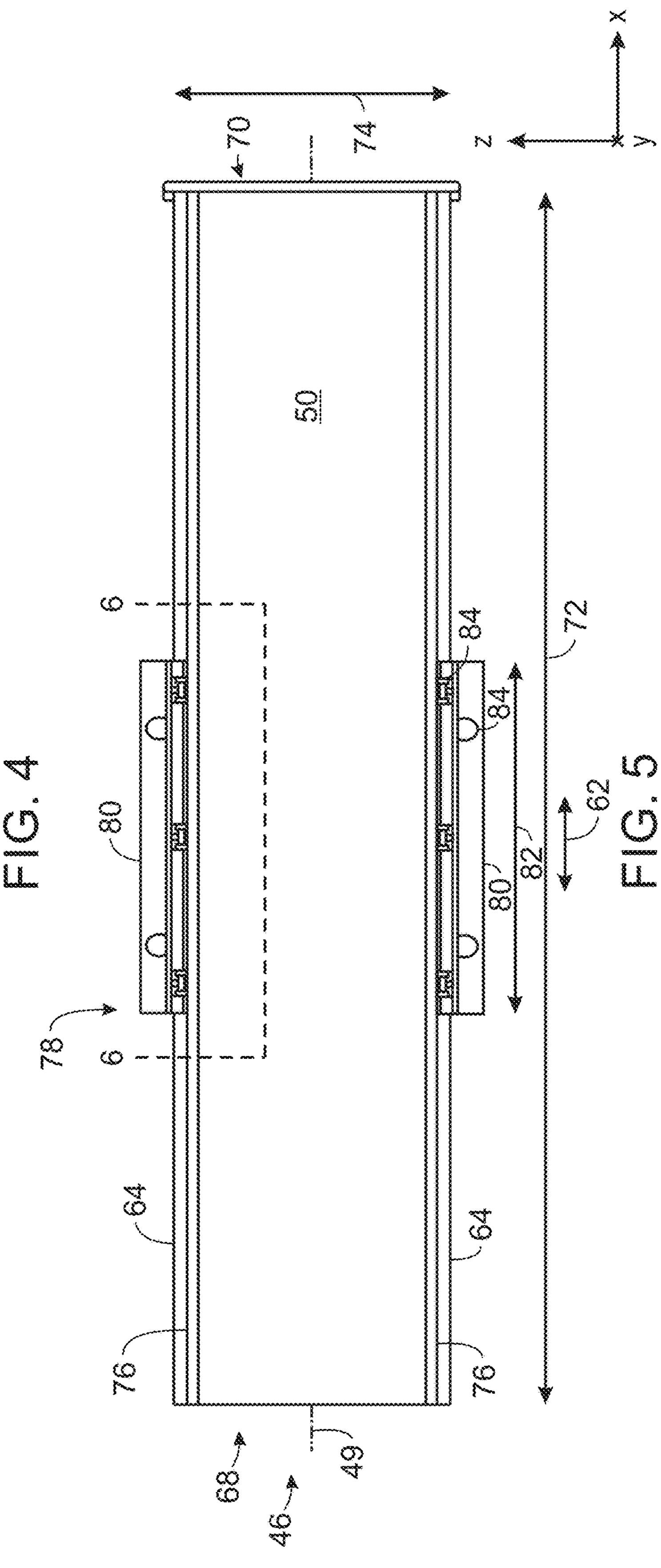
FIG. 5 is a top view of the patient table of the CT imaging system in FIG. 3, in accordance with aspects of the present disclosure.

Although the patient table 46 in the present disclosure is discussed in the context of a CT imaging system, the patient table 46 may be utilized with other types of medical imaging systems (e.g., magnetic resonance imaging system, nuclear medicine imaging system, etc.). Aspects of the patient table 46 in the following figures are discussed utilizing a coordinate system having a y-direction (or y-axis), an x-direction (or x-axis), and a z-direction (or z-axis). The coordinate system may be discussed relative to a longitudinal axis 49 of the patient table 46 (and floating cradle 50). FIGS. 2 and 3 are perspective views of the patient table 46 of the CT imaging system 10 in FIG. 1. FIGS. 4 and 5 are a side view and top view of the patient table 46 of the CT imaging system in FIG. 3, respectively. The patient table 46 includes a base 52. In certain embodiments, the base 52 is fixed to a single location on a floor in a scan room. In other words, the base 52 does not move in the y-direction, the x-direction, and the z-direction. In certain embodiments, the base 52 is configured to move bi-directionally along a path (e.g., extending in the x-direction or axial direction) on the floor in the scan room (e.g., via linear motion guide rails). As depicted, the base 52 is configured to move (e.g., extend and contract) bi-directionally (as indicated by arrow 54) in the y-direction or vertical direction. As depicted, the base 52 includes a plurality of portions 56 that extend and contract relative to each other in the y-direction in a telescopic manner with the largest portion 56 being a at the top and the smallest portion 56 at the bottom. In certain embodiments, the arrangement of the plurality of portions 56 may be inverted and the largest portion 56 may be located on the bottom and the smallest portion at the top. Movement of the base 52 in the y-direction enables the height of the floating cradle 50 to be adjusted relative to the floor.

In certain embodiments, the base 52 may be fixed in the y-direction as depicted in FIG. 3. Thus, the height of the floating cradle 50 cannot be adjusted relative to the floor via the base 52. As depicted in FIG. 3, the base 52 may include a plurality of bars 60 extending in the y-direction, the x-direction, and the z-direction that form the base 52. The structure of the base 52 may vary from that depicted in FIGS. 2 and 3.

The patient table 46 also includes the floating cradle 50. The floating cradle 50 is configured to support a subject (e.g., patient) to be imaged. The floating cradle 50 is configured to move bi-directionally (as indicated by arrow 62) relative to the base 52 in the x-direction and along the longitudinal axis 49. The floating cradle 50 includes a first side 64 and a second side 66 both extending between a first end 68 (first longitudinal end) and a second end 70 (second longitudinal length) in the x-direction. The first end 68 is configured to face the gantry (e.g., gantry 12 of FIG. 1) of the CT imaging system and configured to be moved in and out of the bore of the gantry. The first side 64 and the second side 66 have a length 72 (e.g., longitudinal length) in the x-direction and a width 74 in the z-direction. As depicted in FIG. 2, an entirety of respective edges of the first side 64 and the second side 66 include a step 76.

The patient table 46 further includes a fixed structure 78 coupled to a top of the base 52 (e.g., top portion 58). The fixed structure 78 does not move relative to the top of the base 52 (or the entirety of the base 52 in FIG. 3) in any direction. The fixed structure 78 includes a pair of beams or beam structures 80 (e.g., extruded beams) coupled to the base 52. The pair of beams 80 extend in the x-direction parallel to the longitudinal axis 49. Each beam 80 of the pair of beams has a respective length 82 (e.g., longitudinal length). The length 72 of the floating cradle 50 is greater than the respective length 82 of each beam 80. In certain embodiments, the respective length 82 of each beam 80 may range between approximately 20 percent to 75 percent of the length 72 of the floating cradle 50. The portions of the floating cradle 50 without the base 52 and the fixed structure 78 are considered to be floating (e.g., free of guide rails or any supporting structure). These portions of the floating cradle 50 also guide themselves when extended beyond the fixed structure 78.

The patient table 46 further includes a plurality of rollers 84 mounted to the fixed structure 78. The plurality of rollers 84 is configured both to guide and support the floating cradle 50 as described in greater detail below. In certain embodiments, the plurality of rollers 84 includes a first set of rollers disposed above the floating cradle 50 and a second set of rollers disposed below the floating cradle 50. In certain embodiments, the first set of rollers is configured to retain the floating cradle 50 on the fixed structure. In certain embodiments, the at least one roller of the second set of rollers is configured to support the floating cradle 50 and at least one roller of the second set of rollers is configured to drive movement of the floating cradle 50 bi-directionally (as indicated by arrow 62) relative to the base 52. In certain embodiments, the second set of rollers includes a friction drive roller configured to drive the movement of the floating cradle 50 bi-directionally relative to the base 52 and a pair of rollers flanking the friction drive roller and configured to support the floating cradle 50. In certain embodiments, the second set of rollers includes a roller configured to support the floating cradle 50 and a pair of friction drive rollers flanking the roller and configured to drive the movement of the floating cradle 50 bi-directionally relative to the base 52.

In certain embodiments, the plurality of rollers 84 includes a third set of rollers disposed on the first side 64 and the second side 66 of the floating cradle 50, wherein both the first side 64 and the second side 66 extend between a top surface and a bottom surface of the floating cradle 50. In certain embodiments, at least one roller of the third set of rollers is configured to guide movement of the floating cradle 50 bi-directionally relative to the base 52. In certain embodiments, at least one roller of the third set of rollers is configured to retain the floating cradle 50 on the fixed structure 78. In certain embodiments, at least one roller of the third set of rollers is configured to drive movement of the floating cradle 50 bi-directionally relative to the base 52. In certain embodiments, the third set of rollers includes a first roller disposed on the first side 64 of the floating cradle 50 and a second roller disposed on the second side 66 of the floating cradle 50, and both the first roller and the second roller are configured to drive the movement of the floating cradle 50 bi-directionally relative to the base 52.

Figure 6:
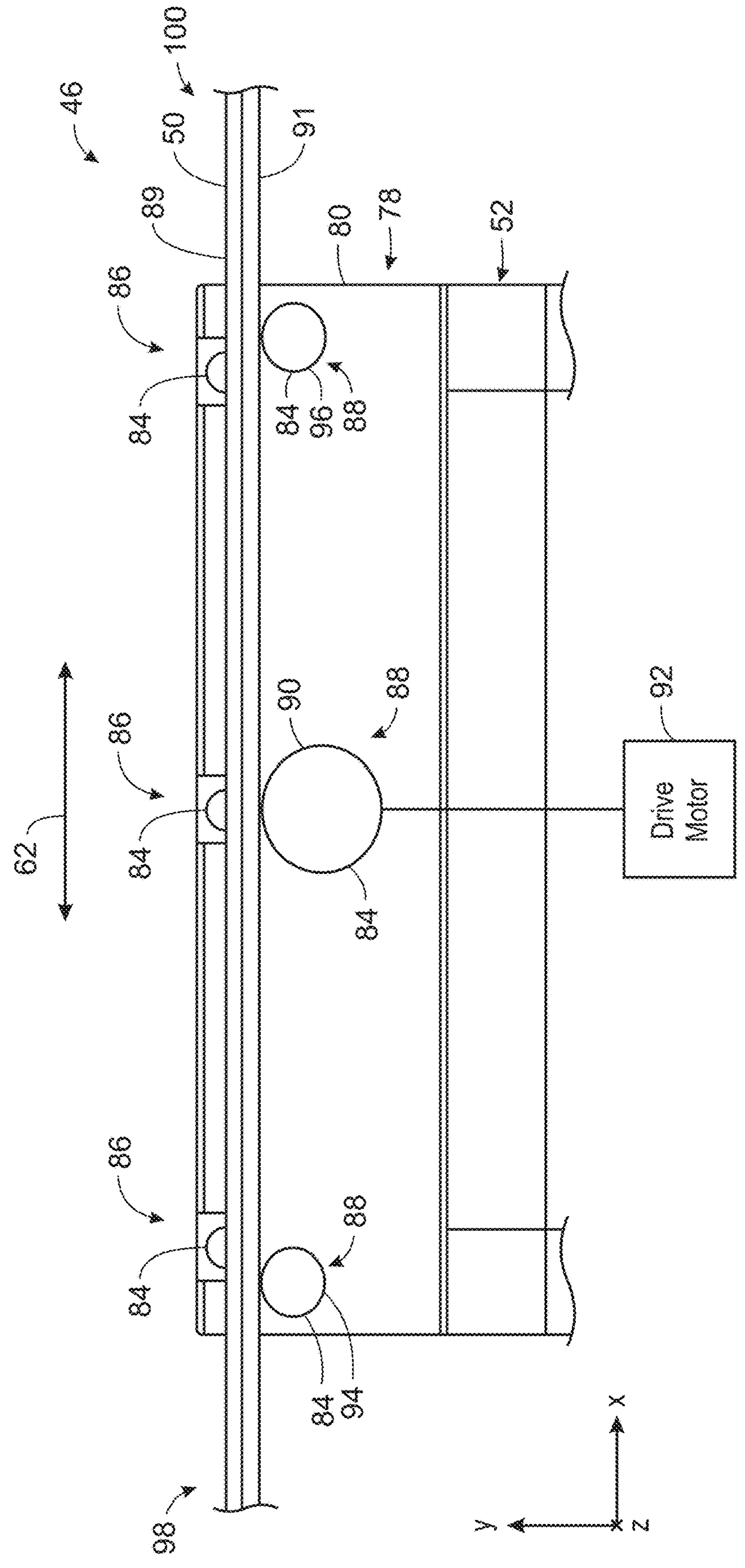
FIG. 6 is a cross-sectional view of the patient table in FIG. 5, taken along line 6-6 (e.g., having flanking support rollers), in accordance with aspects of the present disclosure.

FIG. 6 is a cross-sectional view of the patient table 46 in FIG. 5, taken along line 6-6 (e.g., having flanking support rollers). As noted above, the patient table 46 includes the plurality of rollers 84. The size, position, and number of rollers 84 may vary from that depicted in FIG. 6 to optimize to minimize localized stress on the floating cradle 50. In certain embodiments, each roller 84 may be highly durable rubber coated with a polymer sheath to prevent wear on the floating cradle 50.

As depicted, the plurality of rollers 84 includes a first set 86 of rollers 84 disposed above the floating cradle 50 and a second set 88 of rollers 84 disposed below the floating cradle 50. The first set 86 of rollers 84 contact a top surface 89 of the floating cradle 50. The first set 86 of rollers 84 is configured to retain the floating cradle 50 on the fixed structure 78. In other words, the first set 86 of rollers 84 are load bearing. As depicted, the first set 86 of rollers 84 includes three rollers 84 on each side of the floating cradle 50 (see FIGS. 2-5). However, the number of rollers 84 in the first set 86 of rollers 84 may vary from this.

The second set 88 of rollers 84 contact a bottom surface 91 of the floating cradle 50. At least one roller 84 of the second set 88 of rollers 84 is configured to support the floating cradle 50. Also, at least one roller 84 of the second set 88 of rollers 84 is configured to drive movement of the floating cradle 50 bi-directionally relative to the base. The second set 88 of rollers 84 includes a friction drive roller 90 configured to drive the movement of the floating cradle bi-directionally relative (as indicated by arrow 62) to the base 52. The friction drive roller 90 is coupled to and driven by a drive motor 92. As depicted, the second set 88 of rollers 84 includes a pair of rollers 94, 96 flanking the friction drive roller 90. The pair of rollers 94, 96 are configured to support the floating cradle 50 on the bottom surface 91. The roller 94 is located on a front side 98 (facing the gantry in the CT imaging system) and the roller 96 is located on the rear side 100 (disposed on the opposite side from the gantry). The second set 88 of rollers 84 extend in the z-direction between the pair of beams 80. As depicted, the second set 88 of rollers 84 includes three rollers 84. However, the number of rollers 84 in the second set 88 of rollers 84 may vary from this. In certain embodiments, the second set 88 of rollers 84 includes a roller 84 configured to support the floating cradle 50 and a pair of friction drive rollers flanking the roller 84 and configured to drive the movement of the floating cradle 50 bi-directionally relative to the base 52.

Figure 7:
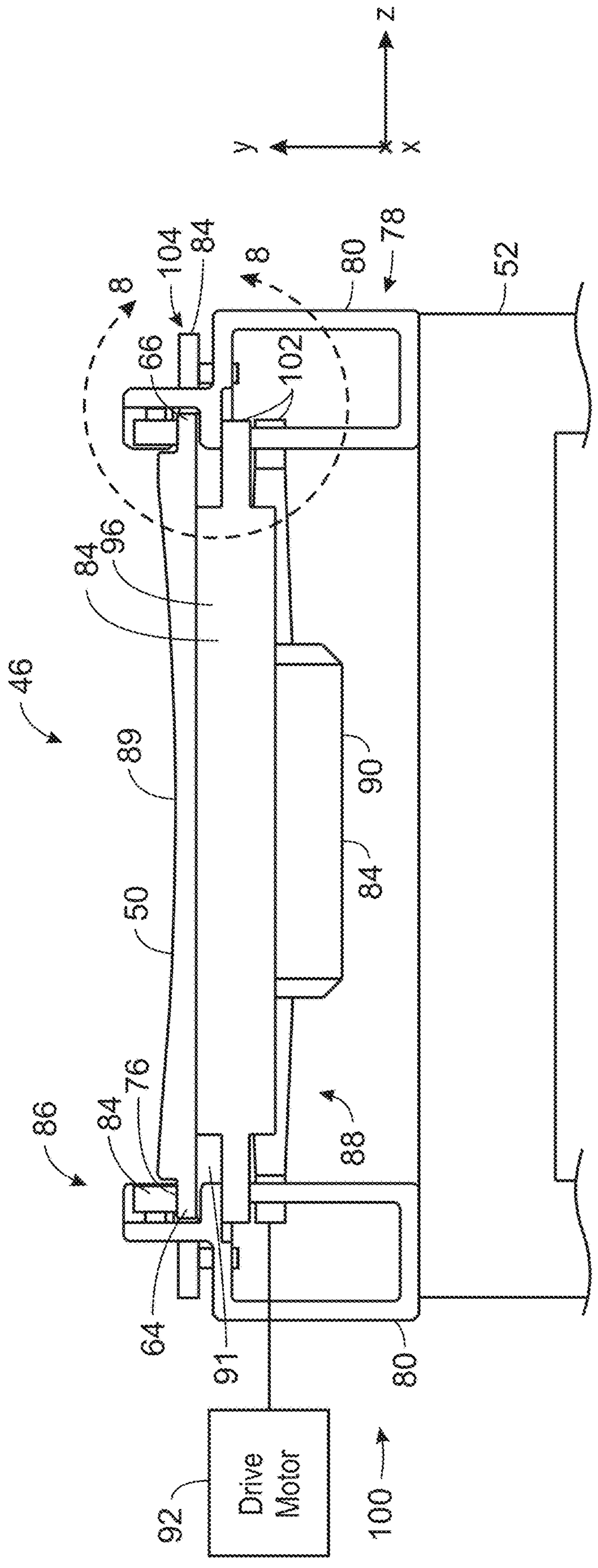
FIG. 7 is a cross-sectional view of the patient table in FIG. 4, taken along line 7-7 (e.g., with a floating cradle having a step along a side), in accordance with aspects of the present disclosure.
Figure 8:
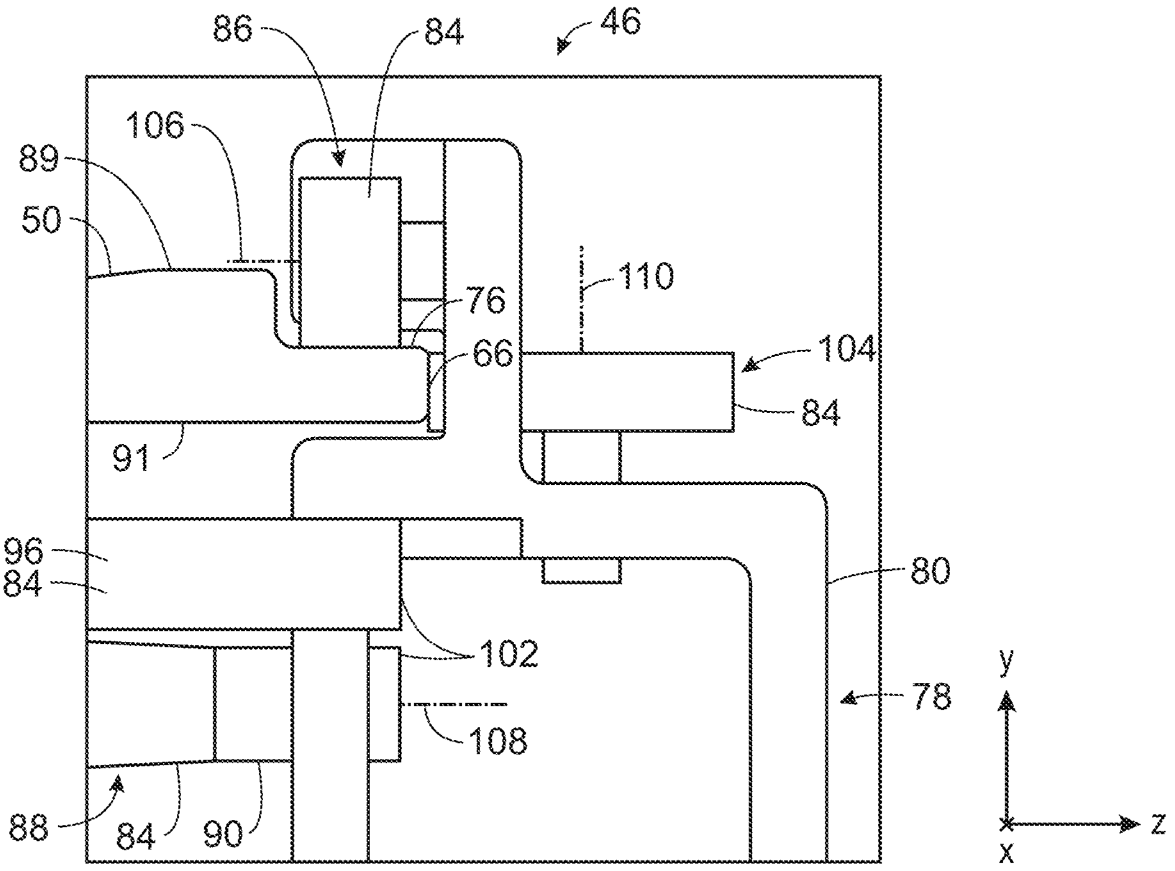
FIG. 8 is a cross-sectional view of the patient table in FIG. 7, taken with line 8-8, in accordance with aspects of the present disclosure.

FIG. 7 is a cross-sectional view of the patient table 46 in FIG. 4, taken along line 7-7. FIG. 8 is a cross-sectional view of the patient table 46 in FIG. 7, taken with line 8-8. The first set 86 of rollers 84 and the second set 88 of rollers 84 are as described in FIG. 6. As depicted in FIGS. 7 and 8, respective ends 102 (longitudinal ends) of each roller 84 of the second set 88 of rollers 84 extend into the respective beams 80 of the pair of beams 80. In addition, the first set 86 of rollers 84 contact the top of the floating cradle 50 on the steps 76 disposed along the edges adjacent the first side 64 and the second side 66.

Also, the plurality of rollers 84 includes a third set 104 of rollers 84. The third set 104 of rollers 84 disposed on a first side 64 and second side 66 of the floating cradle 50. Both the first side 64 and the second side 66 extend between the top surface 89 and the bottom surface 91 of the floating cradle 50. The third set 104 of rollers 84 is configured to guide movement of the floating cradle 50 bi-directionally relative to the base 52. As depicted, the rollers 84 of the third set 104 of rollers contact the respective sides 64, 66 of the floating cradle 50. The third set 104 of rollers 84 includes two rollers 84 on each side 64, 66 of the floating cradle 50 (see FIGS. 2-5). However, the number of rollers 84 in the third set 104 of rollers 84 on the each side 64, 66 of the floating cradle 50 may vary from this.

In certain embodiments, at least one roller 84 of the third set 104 of rollers 84 is configured to retain the floating cradle 50 on the fixed structure 78. In certain embodiments, at least one roller 84 of the third set 104 of rollers 84 is configured to drive movement of the floating cradle 50 bi-directionally relative to the base 52. In certain embodiments, the third set 104 of rollers 84 includes a first roller 84 on disposed on the first side 64 of the floating cradle 50 and a second roller 84 disposed on the second side 66 of the floating cradle 50, and both the first roller 84 and the second roller 84 are configured to drive the movement of the floating cradle 50 bi-directionally relative to the base 52.

As depicted in FIG. 8, each roller 84 of the first set 86 of rollers 84 has a rotational axis 106 extending in the z-direction. Each roller 84 of the second set 88 of rollers 84 has a rotational axis 108 also extending in the z-direction. Each roller 84 of the third set 104 of rollers 84 has a rotational axis 110 extending in the y-direction. The respective rotational axes of the different sets of rollers 84 may vary from this in certain embodiments.

Figure 9:
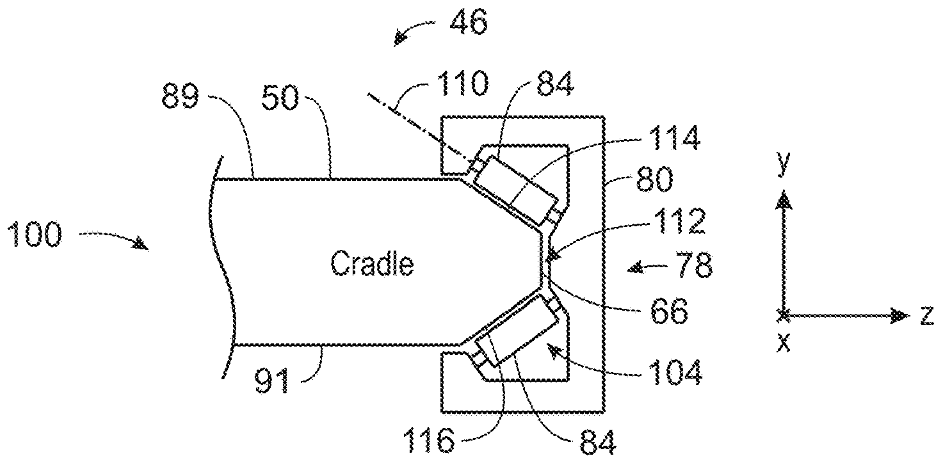
FIG. 9 is a cross-sectional view of the patient table in FIG. 4, taken along line 7-7 (e.g., with a floating cradle having a tapered side), in accordance with aspects of the present disclosure.
Figure 10:
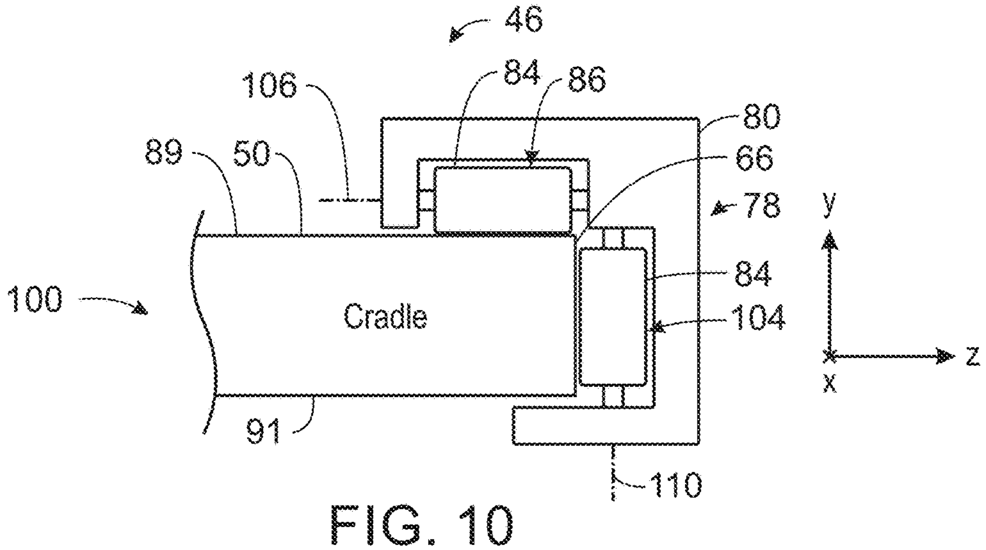
FIG. 10 is a cross-sectional view of the patient table in FIG. 4, taken along line 7-7 (e.g., with a floating cradle lacking a step on the side), in accordance with aspects of the present disclosure.
Figure 11:
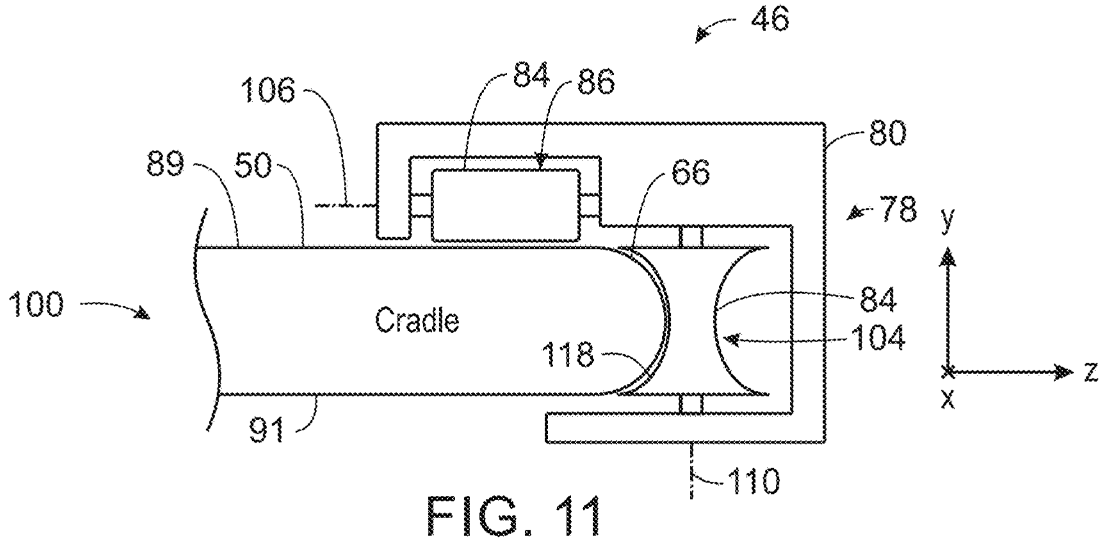
FIG. 11 is a cross-sectional view of the patient table in FIG. 4, taken along line 7-7 (e.g., with a floating cradle having rounded sides), in accordance with aspects of the present disclosure.

FIGS. 9-11 are alternative arrangements for rollers 84 when the shape of the floating cradle 50 varies on the sides 64. 66. Although the arrangements for the rollers 84 are only depicted for the second side 66 of the floating cradle 50, these arrangements may also be utilized on the first side 64 of the floating cradle 50. FIG. 9 is a cross-sectional view of the patient table in FIG. 4, taken along line 7-7. As depicted in FIG. 9, the side 66 of the floating cradle 50 has a tapered end 112. The tapered end 112 has a top surface 114 and a bottom surface 116. One or more rollers 84 of the third set 104 of rollers 84 contact the top surface 114 of the tapered end 112. One or more rollers 84 of the third set 104 of rollers 84 also contact the bottom surface 116 of the tapered end 112. Each roller 84 of the third set 104 of rollers 84 contacting the tapered end 112 (top surface 114 or bottom surface 116) is configured both to retain the floating cradle 50 on the fixed structure and to guide movement of the floating cradle 50 bi-directionally relative to the base. As depicted, the rotational axis 110 of each roller 84 of the third set 104 of rollers 84 is parallel with the surface (e.g., top surface 114 or bottom surface 116) of the tapered end 112 contacted by the respective roller 84.

FIG. 10 is a cross-sectional view of the patient table 46 in FIG. 4, taken along line 7-7. As depicted in FIG. 9, the side 66 of the floating cradle 50 lacks a step (i.e., is rectilinear). One or more rollers 84 of the first set 86 of rollers 84 contact the top surface 89 of the floating cradle 50. Each roller 84 of the first set 86 of rollers 84 is configured to retain the floating cradle 50 on the fixed structure. One or more rollers 84 of the second set 88 of rollers 84 contact the top surface 114 of the tapered end 112. One or more rollers 84 of the third set 104 of rollers 84 contact the side 66. Each roller 84 of the third set 104 of rollers 84 is configured to guide movement of the floating cradle 50 bi-directionally relative to the base. As depicted, the rotational axis 106 of each roller 84 of the first set 86 of rollers 84 extends in the z-direction. Also, as depicted, the rotational axis 110 of each roller 84 of the third set 104 of rollers 84 is extends in the y-direction.

FIG. 11 is a cross-sectional view of the patient table 46 in FIG. 4, taken along line 7-7. As depicted in FIG. 9, the side 66 of the floating cradle 50 is rounded. One or more rollers 84 of the first set 86 of rollers 84 contact the top surface 89 of the floating cradle 50. Each roller 84 of the first set 86 of rollers 84 is configured to retain the floating cradle 50 on the fixed structure. One or more rollers 84 of the second set 88 of rollers 84 contact the top surface 114 of the tapered end 112. One or more rollers 84 of the third set 104 of rollers 84 contact the side 66. In particular, each roller 84 of the third set of rollers has a concave surface 118 to correspond with the rounded side 66. Each roller 84 of the third set 104 of rollers 84 is configured to guide movement of the floating cradle 50 bi-directionally relative to the base. As depicted, the rotational axis 106 of each roller 84 of the first set 86 of rollers 84 extends in the z-direction. Also, as depicted, the rotational axis 110 of each roller 84 of the third set 104 of rollers 84 extends in the y-direction.

Figure 12:
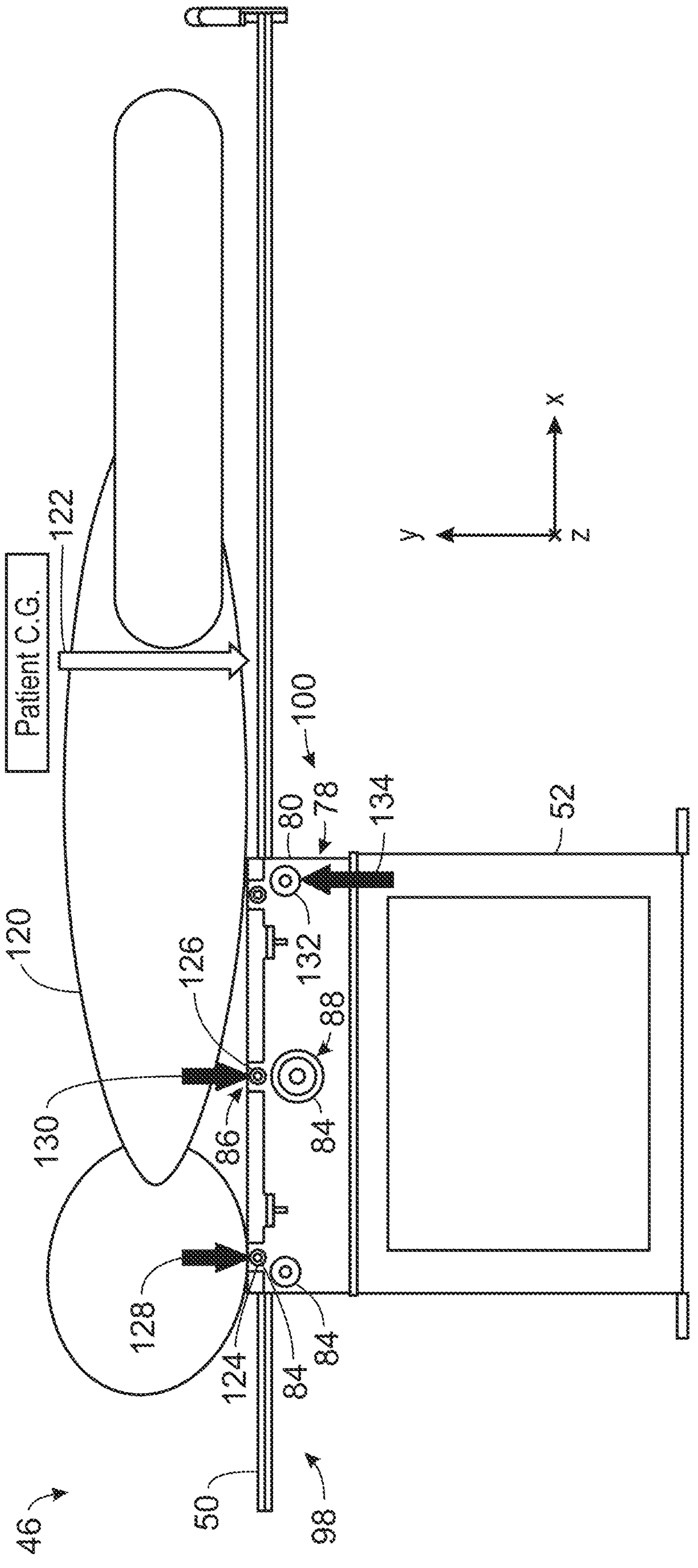
FIG. 12 is a schematic view of the patient table in FIG. 3 with a patient disposed on a floating cradle (e.g., with the floating cradle outside of a gantry), in accordance with aspects of the present disclosure.

FIG. 12 is a schematic view of the patient table 46 in FIG. 3 with a patient 120 (e.g., subject) disposed on the floating cradle 50. As depicted in FIG. 12, the floating cradle 50 is in a home position with both the patient 120 and the floating cradle 50 outside of a gantry (not shown) of the CT imaging system. In the home position, a majority of the floating cradle 50 is located to the rear 100 of the base 52 and the fixed structure 78. Also, a center of gravity of the patient 120 (indicated by arrow 122) is also located to the rear 100 of the base 52 and the fixed structure 78. This causes a front roller 124 and a middle roller 126 of the first set 86 of rollers 84 to act as load bearing and to retain the floating cradle 50 on the fixed structure 78 as indicated by arrows 128, 130, respectively. This also causes a rear roller 132 of the second set 88 of rollers 84 to support the floating cradle 50 as indicated by arrow 134.

Figure 13:
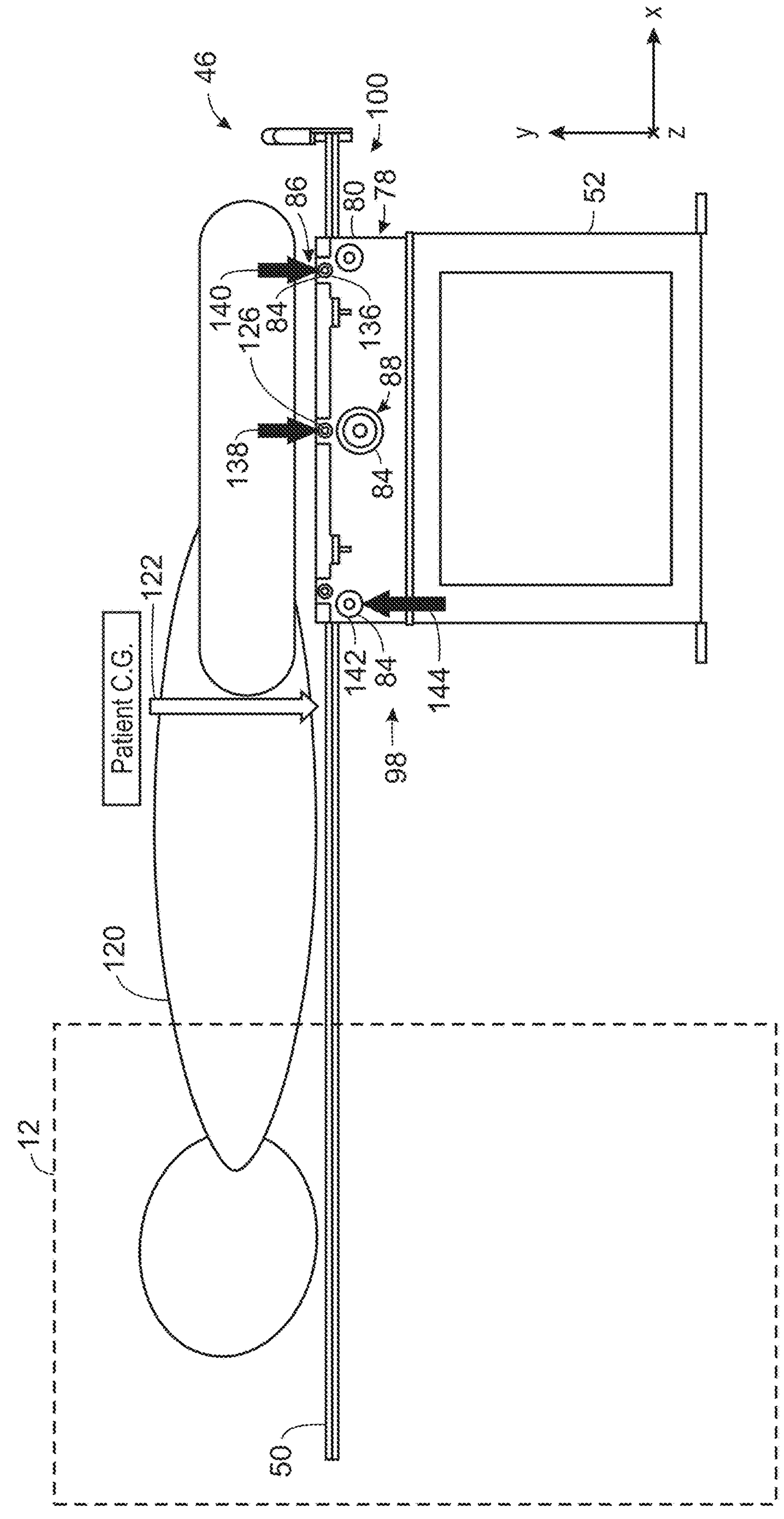
FIG. 13 is a schematic view of the patient table in FIG. 3 with a patient disposed on a floating cradle (e.g., with the floating cradle inside of a gantry), in accordance with aspects of the present disclosure.

FIG. 13 is another schematic view of the patient table 46 in FIG. 3 with the patient disposed on the floating cradle 50. As depicted in FIG. 13, the patient 120 is in scan range with both a portion of the patient 120 and a portion of the floating cradle 50 located inside the gantry 12 of the CT imaging system. With the portion of the patient 120 and the portion of the floating cradle 50 located inside the gantry 12, a majority of the floating cradle 50 is located to the front 98 of the base 52 and the fixed structure 78. Also, the center of gravity 122 of the patient 120 is also located to the front 98 of the base 52 and the fixed structure 78. This causes a middle roller 126 and a rear roller 136 of the first set 86 of rollers 84 to act as load bearing and to retain the floating cradle 50 on the fixed structure 78 as indicated by arrows 138, 140, respectively. This also causes a front roller 142 of the second set 88 of rollers 84 to support the floating cradle 50 as indicated by arrow 144.

Figure 14:
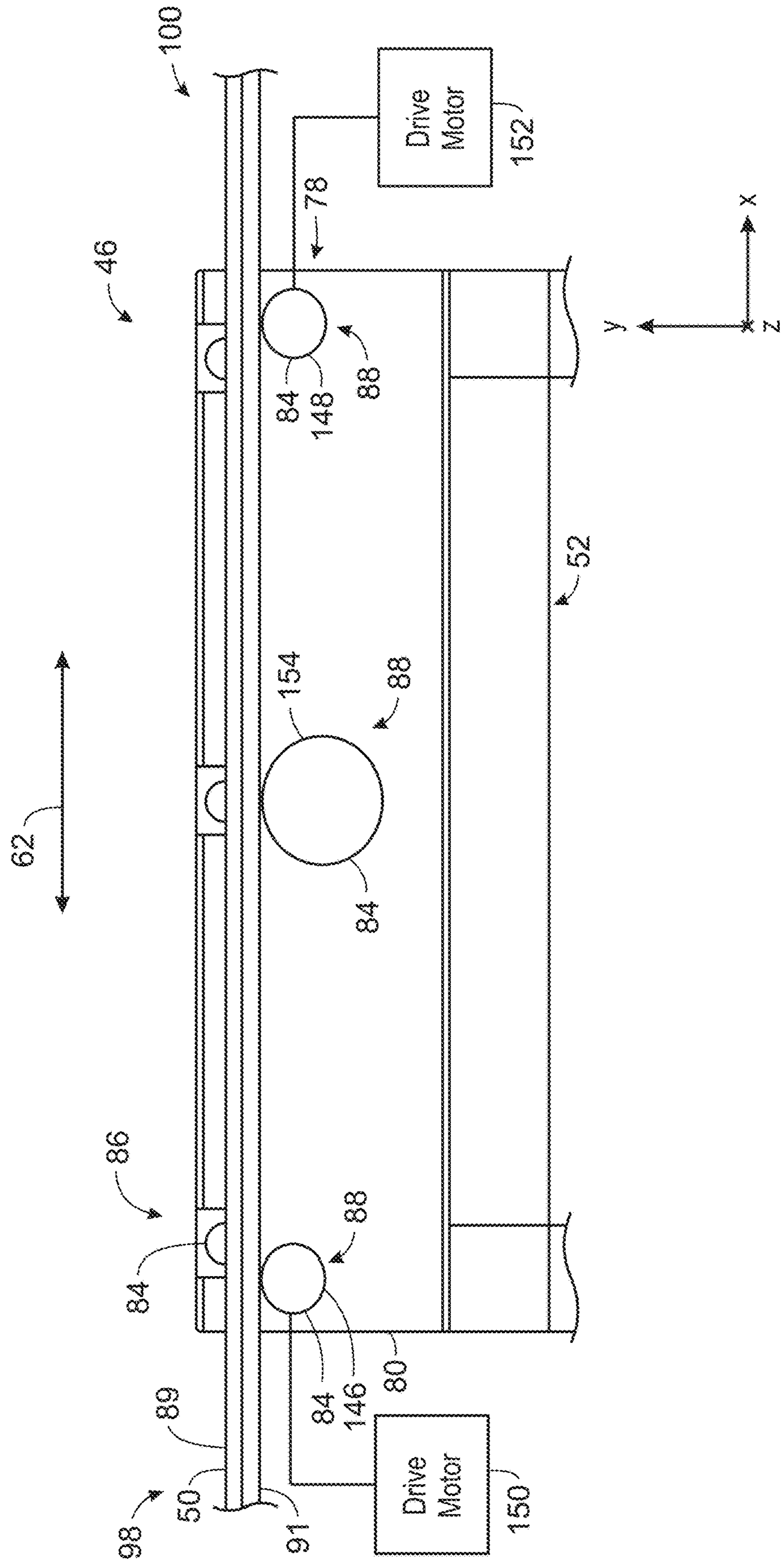
FIG. 14 is a cross-sectional view of the patient table in FIG. 5, taken along line 6-6 (e.g., having flanking drive rollers), in accordance with aspects of the present disclosure.

FIG. 14 is a cross-sectional view of the patient table 46 in FIG. 5, taken along line 6-6 (e.g., having flanking drive rollers). The structure of the patient table 46 in FIG. 14 is similar to that in FIG. 6 with the exception of the second set 88 of rollers 84. The second set 88 of rollers 84 contact the bottom surface 91 of the floating cradle 50. A pair of friction drive rollers 146, 148 of the second set 88 of rollers 84 are configured to drive (via dual synchronous friction drive) the movement of the floating cradle 50 bi-directionally (as indicated by arrow 62) relative to the base 52. This may provide better cradle traction. The friction drive roller 146 is located adjacent the front 98 of the fixed structure 78. The friction drive roller 148 is located adjacent the rear 100 of the fixed structure 78. Each friction drive roller 146, 148 is coupled to and driven by a respective drive motor 150, 152. The second set 88 of rollers 84 also includes roller 154. The roller 154 is centrally located between and flanked by the pair of friction drive rollers 146, 148.

Figure 15:
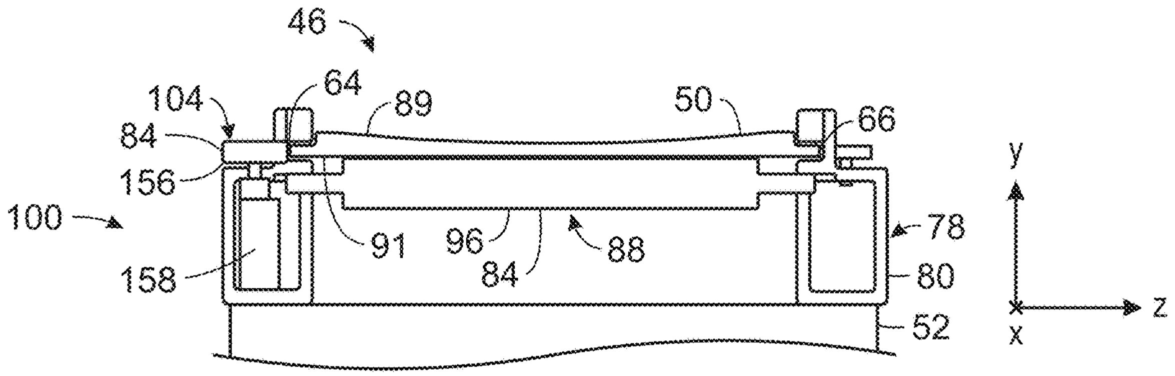
FIG. 15 is a cross-sectional view of the patient table in FIG. 4, taken along line 7-7 (e.g., having a drive roller on a side of a floating cradle), in accordance with aspects of the present disclosure.

FIG. 15 is a cross-sectional view of the patient table 46 in FIG. 4, taken along line 7-7 (e.g., having a drive roller on a side of the floating cradle 50). In certain embodiments, as depicted in FIG. 15, each roller 84 of the second set 88 of rollers 84 (e.g., roller 96) is configured to contact the bottom surface 91 of the floating cradle 50 and to support the floating cradle 50. In addition, as depicted in FIG. 15, the third set 104 of rollers 84 includes a friction drive roller 156 (e.g., contacting the first side 64 of the floating cradle 50) configured to drive movement of the floating cradle 50 bi-directionally relative to the base 52. The friction drive roller 156 is coupled to and driven by a drive motor 158. In certain embodiments, other rollers 84 of the third set 104 of rollers 84 may be configured to guide movement of the floating cradle 50 bi-directionally relative to the base 52.

Figure 16:
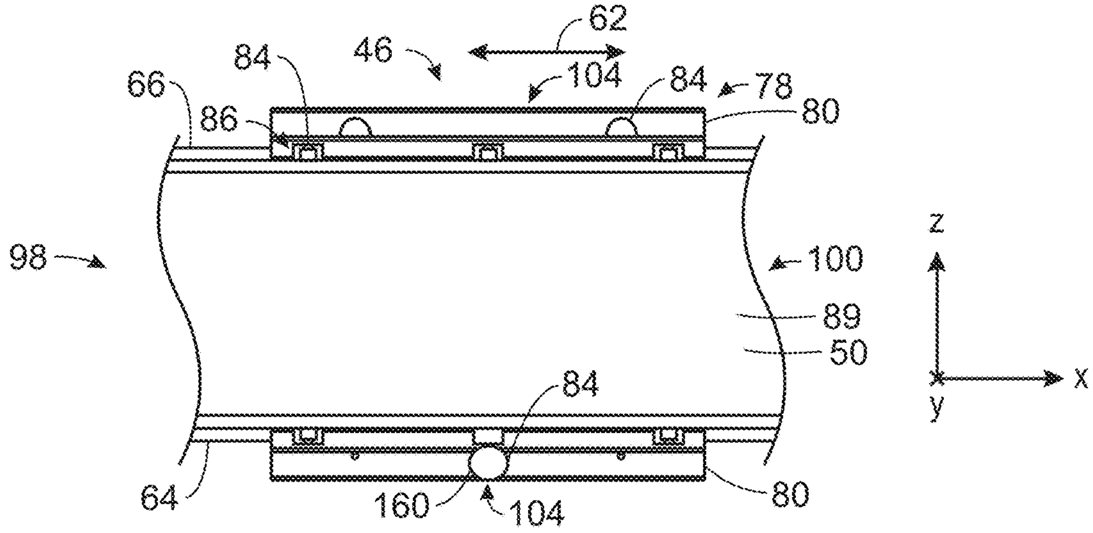
FIG. 16 is a top view of a portion of the patient table of the CT imaging system in FIG. 4 (e.g., having single friction drive), in accordance with aspects of the present disclosure.

FIG. 16 is a top view of a portion of the patient table 46 of the CT imaging system in FIG. 4 (e.g., having single friction drive). As depicted in FIG. 16, the third set 104 of rollers 84 includes a single roller 84 disposed on and contacting the first side 64 of the floating cradle 50. This single roller 84 is a friction drive roller or wheel 160 (driven by a drive motor) configured to drive movement of the floating cradle 50 bi-directionally (as indicated by arrow 62) relative to the base. The third set 104 of rollers 84 also includes a pair of rollers 84 disposed on and contacting the second side 66 of the floating cradle 50. The pair of roller 84 on the second side 66 of the floating cradle 50 are configured to guide movement of the floating cradle 50 bi-directionally relative to the base.

Figure 17:
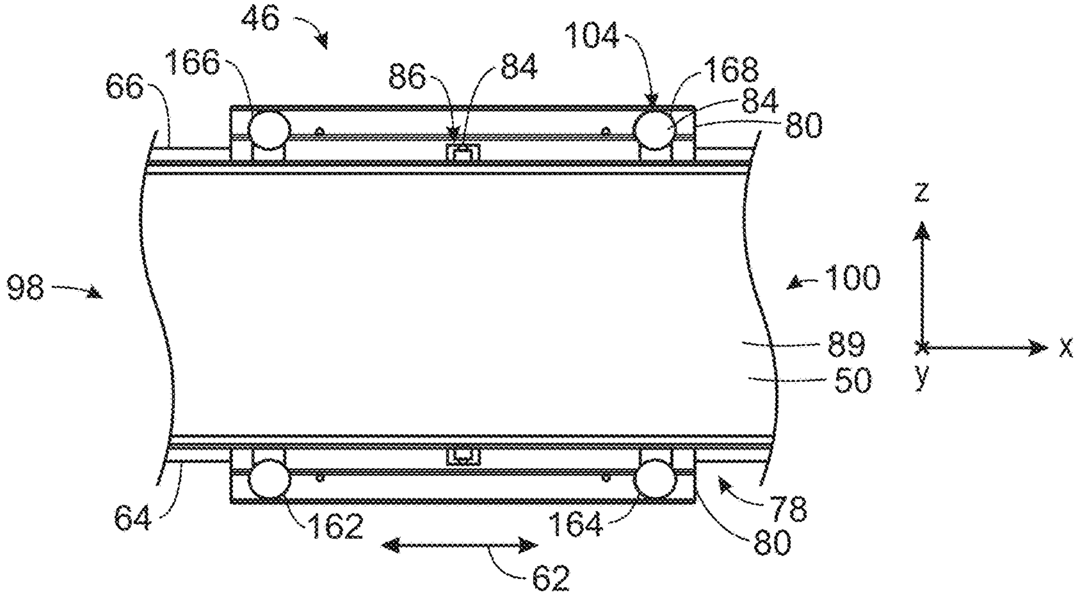
FIG. 17 is a top view of a portion of the patient table of the CT imaging system in FIG. 4 (e.g., having multiple synchronous friction drive), in accordance with aspects of the present disclosure.

FIG. 17 is a top view of a portion of the patient table 46 of the CT imaging system in FIG. 4 (e.g., having multiple synchronous friction drive). As depicted in FIG. 17, the third set 104 of rollers 84 includes a pair of friction drive rollers or wheels 162, 164 disposed on and contacting the first side 64 of the floating cradle 50. The third set 104 of rollers 84 also includes a pair of friction drive rollers or wheels 166, 168 disposed on and contacting the second side 66 of the floating cradle 50. The friction drive rollers 162, 164, 166, 168 (driven by respective drive motors) are configured to drive movement of the floating cradle 50 bi-directionally (as indicated by arrow 62) relative to the base. This configuration enables multiple synchronous friction drive on both sides 64, 66 of the floating cradle 50.

In certain embodiments, the friction drive rollers in FIGS. 15-17 may each be spring-loaded to have high pressure contact against the floating cradle 50 at all times during movement of the floating cradle 50 to avoid traction loss. In certain embodiments, a housing associated with each friction driver roller may be configured to safeguard the patient from pinching by the friction drive roller.

Figure 18:
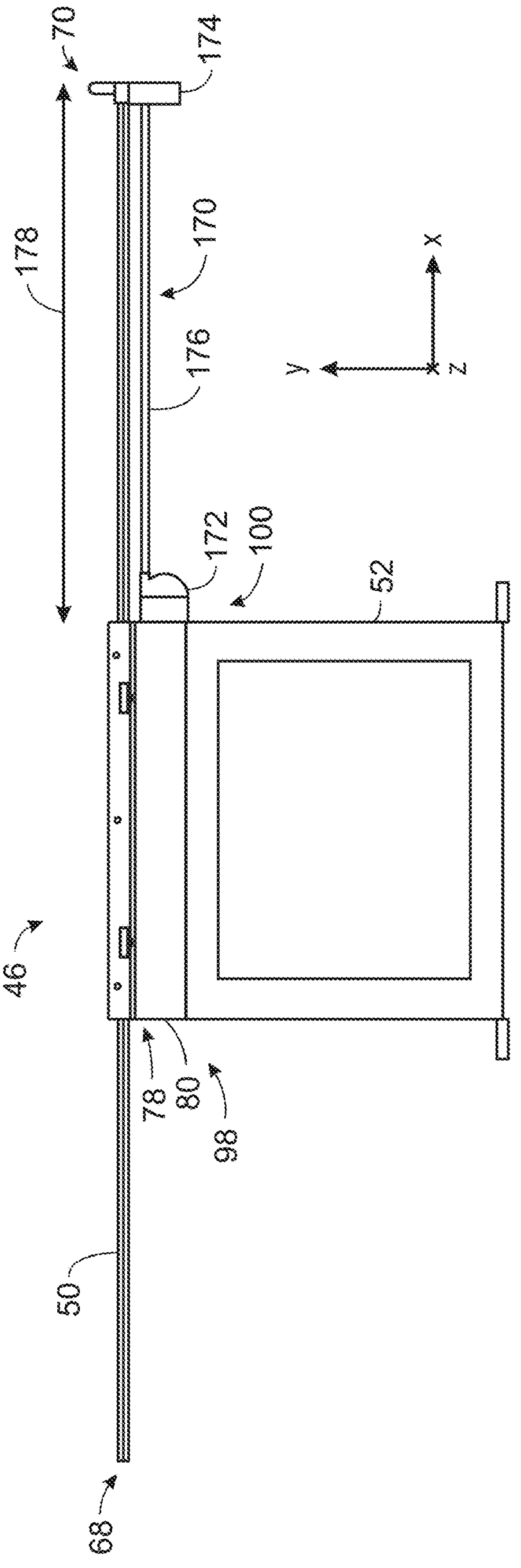
FIG. 18 is a side view of the patient table of the CT imaging system in FIG. 3 (e.g., having an adjustable cable retractor), in accordance with aspects of the present disclosure.

In certain embodiments, the home position of the floating cradle 50 (i.e., position when floating cradle 50 is not disposed within the gantry) may be adjustable. FIG. 18 is a side view of the patient table 46 of the CT imaging system in FIG. 3. The patient table 46 includes a cable retractor 170 (e.g., adjustable cable retractor). The cable retractor 170 includes a first end structure 172 coupled to the fixed structure 78 (e.g., at the rear 100). The cable retractor 170 also includes a second end structure 174 coupled to the longitudinal end 70 of the floating cradle 50. The cable retractor 170 further includes a cord 176 extending between the first end structure 172 and the second end structure 174. The first end structure 172 serves as a housing for the cord 176 and also includes a torsion spring to that provides tension to the cord 176 when coupled to the longitudinal end 70. The cable retractor 170 is configured to keep the longitudinal end 70 of the floating cradle 50 from extending beyond a fixed or set distance 178 from the fixed structure 78. The cable retractor 170 is also configured to be adjusted to change or to set the fixed distance 178 based on the scan room size. The cable retractor 170 enables the home position of the floating cradle 50 to be maintained with a hard stop.

Figure 19:
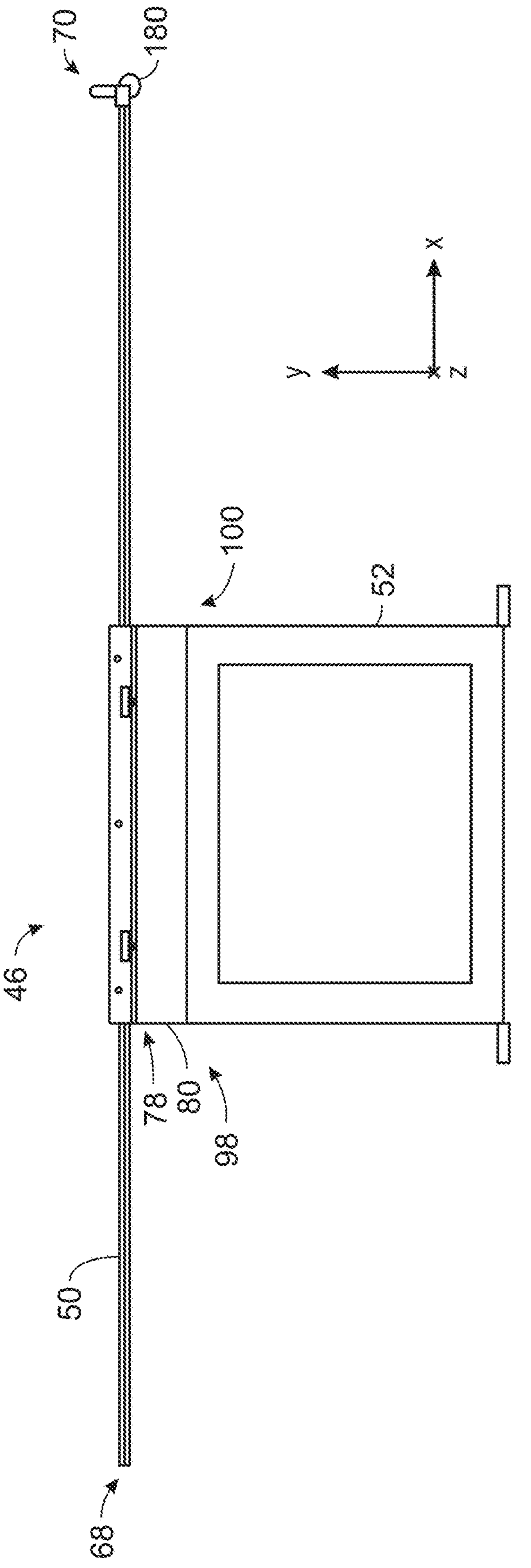
FIG. 19 is a side view of the patient table of the CT imaging system in FIG. 3 (e.g., having an anti-collision sensor), in accordance with aspects of the present disclosure.

FIG. 19 is a side view of the patient table 46 of the CT imaging system in FIG. 3. The patient table 46 includes a sensor 180 (e.g., anti-collision sensor) coupled to the longitudinal end 70 of the floating cradle 50. The sensor 180 is configured to sense an object (e.g., person, wall, etc.) and to send a signal (e.g., to the table motor controller 44 in FIG. 1) to stop movement of the floating cradle 50 in the z-direction to avoid collision with the object. In certain embodiments, another sensor 180 may be disposed on the longitudinal end 68 of the floating cradle 50.

Figure 20:
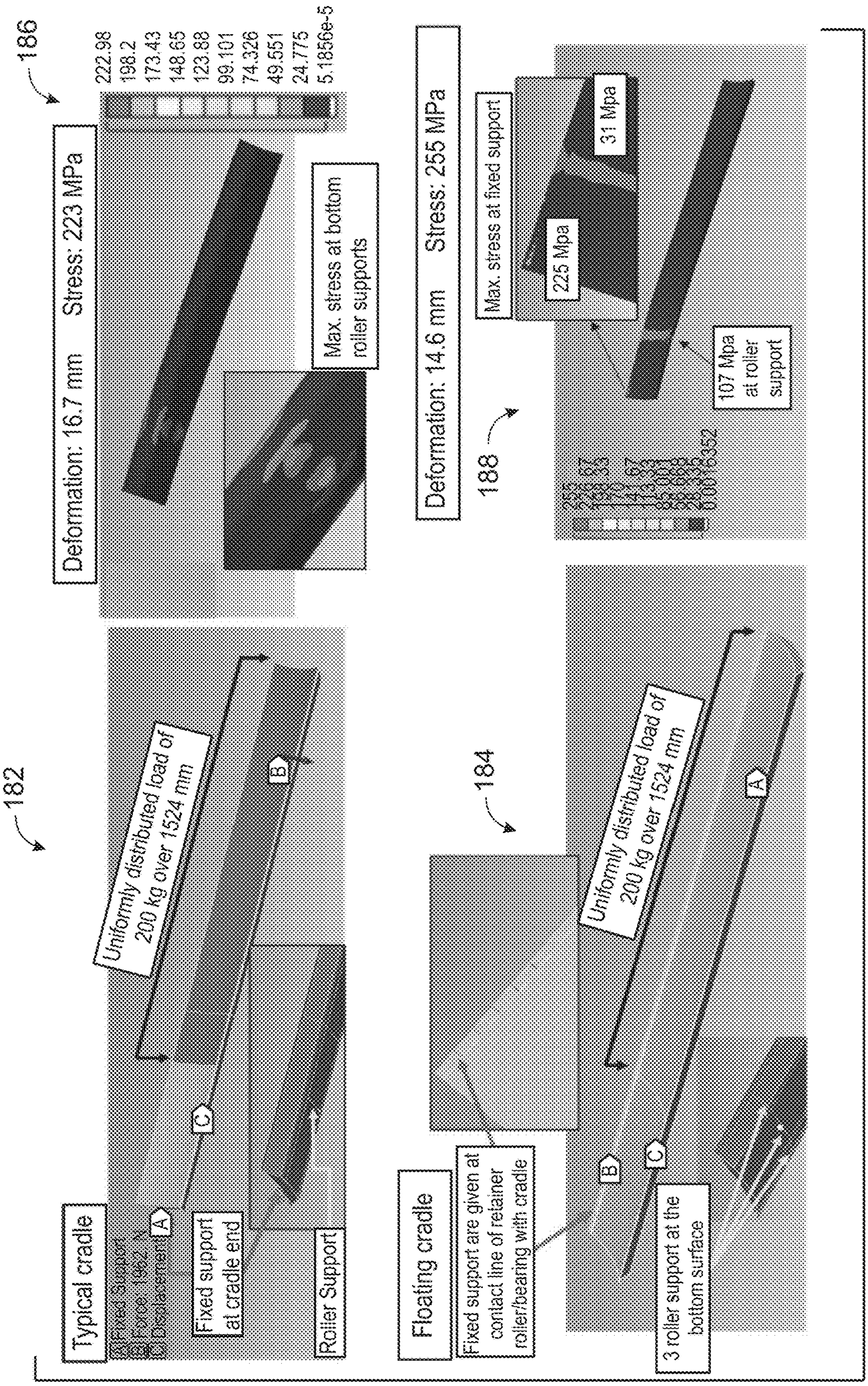
FIG. 20 depicts images comparing stress analysis of a typical cradle to a floating cradle.

FIG. 20 depicts images comparing stress analysis of a typical cradle to a floating cradle. Image 182 indicates where the support is provided on the typical cradle. As depicted in the image 182, a fixed support is provided at one end of the cradle with roller support underneath. Image 184 indicates where support is provided on the floating cradle. As depicted in the image 184, fixed support is given at the contact lines of retainer rollers along the sides of the floating cradle as described above. Also, three rollers provide support on the bottom surface of the floating cradle as described above. Images 186 and 188 are the stress plots for the typical cradle and the floating cradle, respectively. As depicted in images 186 and 188, for a similar load condition and cradle cross-section, deflection and stresses in the floating cradle are similar to those in the typical cradle.

Figure 21:
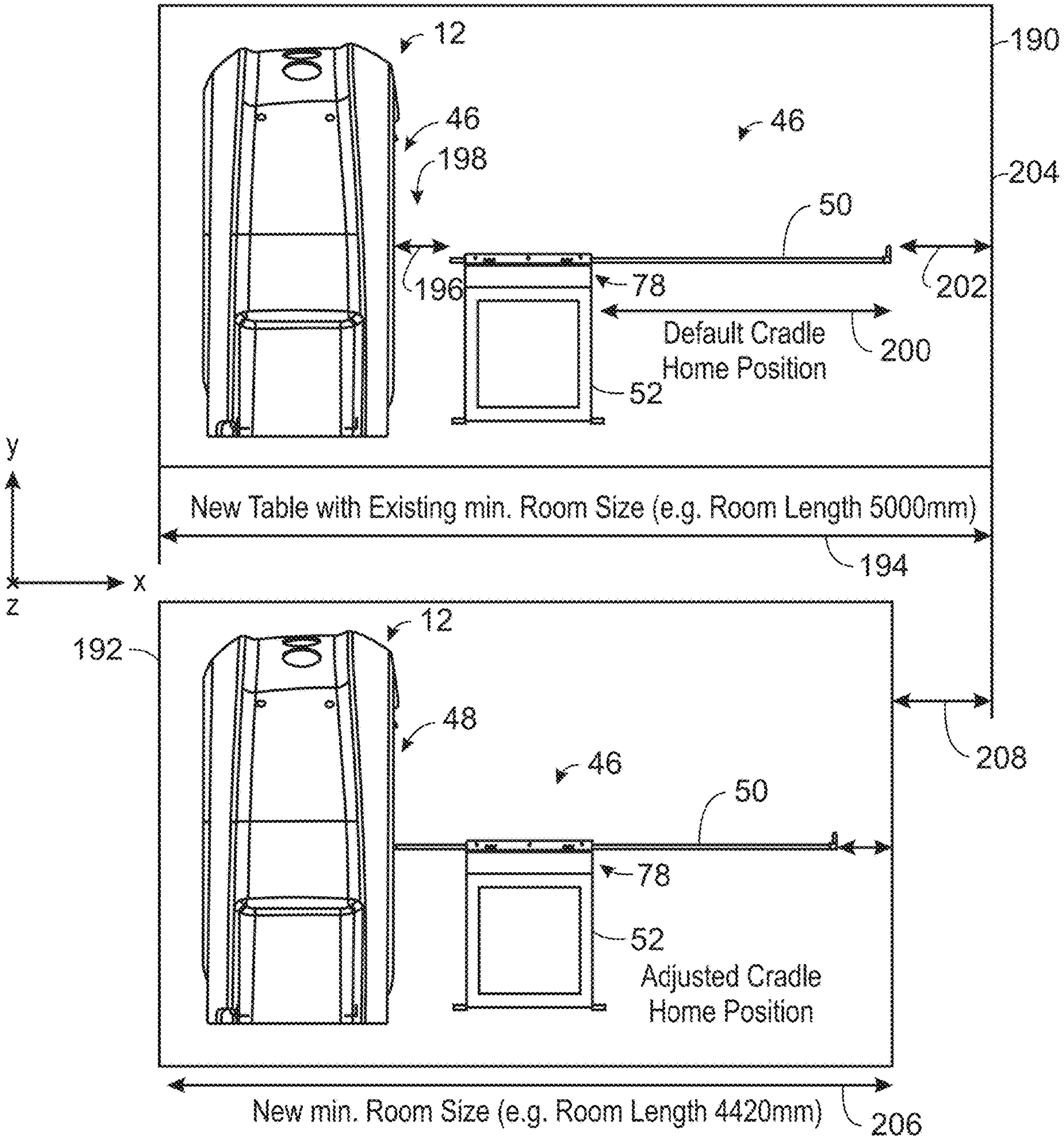
FIG. 21 is a schematic view of a CT scanner and the patient table in FIG. 3 in a scan room sized for a typical patient table and a smaller scan room enabled by the patient table in FIG. 3, in accordance with aspects of the present disclosure.

FIG. 21 is a schematic view of a CT scanner (e.g., gantry 12) and the patient table 46 in FIG. 3 in a scan room 190 sized for a typical patient table and a smaller scan room 192 enabled by the patient table 46 in FIG. 3. As noted above, the patient table 46 includes an adjustable cradle home position. The scan room 190 has a room length 194 of approximately 5000 millimeters (mm). In the scan room 190, during service, the floating cradle 50 can be pulled back (i.e., away from the gantry 12 in the x-direction) by a first distance 196 to create a gap 198 between the gantry 12 and the patient table 46. The first distance 196 may be up to approximately 205 mm given the room length 194. The floating cradle 50 is pulled back to a default cradle home position indicated by arrow 200. In the scan room 190, a second distance 202 of the floating cradle 50 (in the default cradle home position) and the wall 204 may be up to approximately 580 millimeters. However, if the operator needs to access space between the wall 204 and the floating cradle 50, a portion of the floating cradle can be moved into an opening 48 of the gantry by a certain distance in the x-direction. Further, with the provision of the adjustable cradle home position, the patient table 46 may be disposed and utilized in a smaller scan room (e.g., scan room 192). The scan room 192 has a room length that provides a distance saving (as indicated by arrow 208) of approximately 580 mm. The distances noted in FIG. 21 may vary based on the patient table size and the size of the CT scanner within a scan room.

Figure 22:
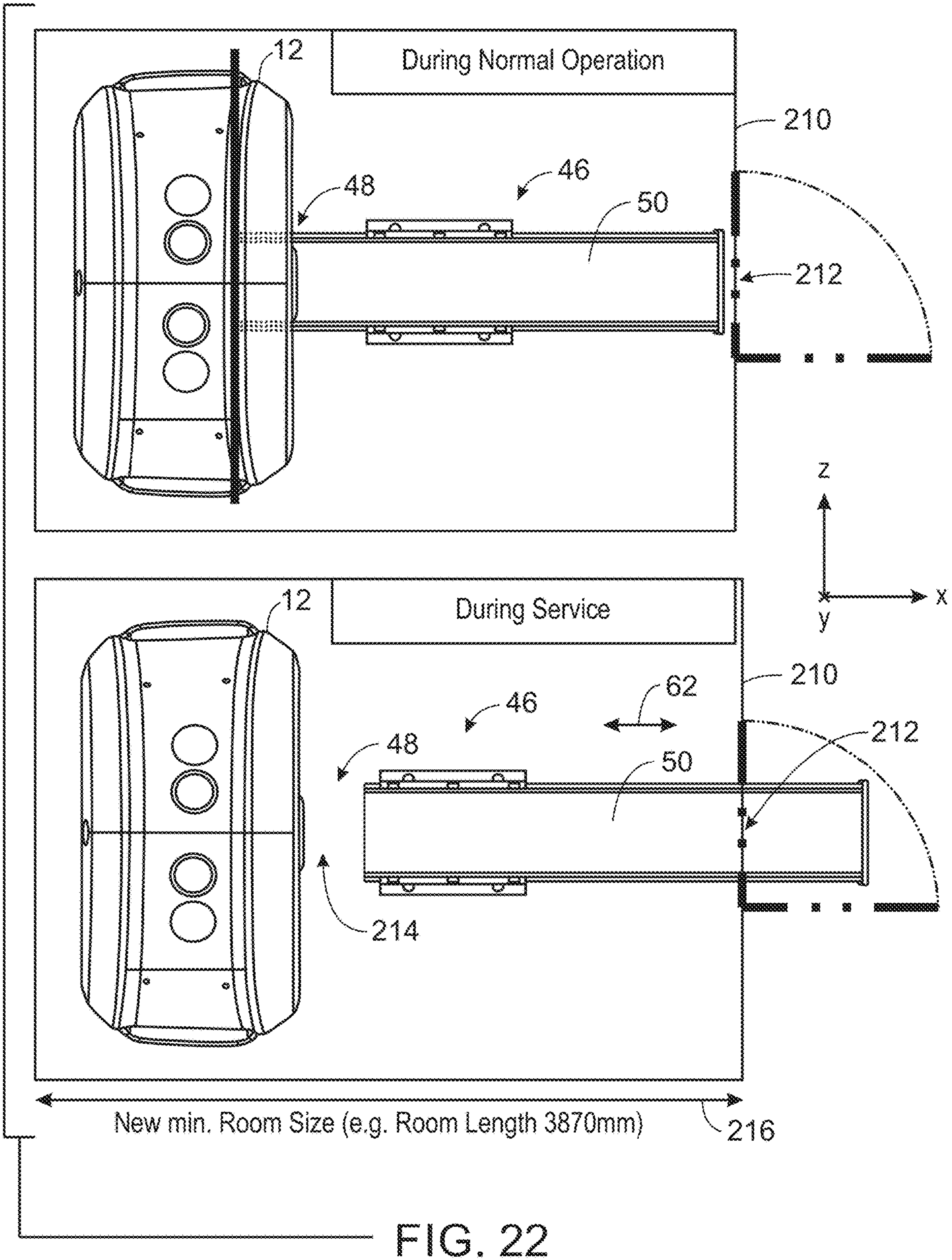
FIG. 22 is a schematic view of a CT scanner and the patient table in FIG. 3 in a scan room (e.g., during normal operation and during service), in accordance with aspects of the present disclosure.

The scan room size can be further reduced utilizing the patient table 46 in FIG. 3 if disposed adjacent to a door of the scan room. FIG. 22 is a schematic view of a CT scanner (e.g., gantry 12) and the patient table 46 in FIG. 3 in a scan room 210 (e.g., during normal operation and during service). As depicted in FIG. 22, the patient table is arranged in the scan room 210 so that the floating cradle 50 can be moved bi-directionally (as indicated by arrow 62) so that the floating cradle 50 can be moved into gantry 12 or through a door opening 212. The top portion of FIG. 22 depicts a portion of the floating cradle 50 being disposed within the opening 48 of the gantry 12 during normal operation. The bottom portion of FIG. 22 depicts a portion of the floating cradle 50 being moved through the door opening 212 during service to create a gap 214 between the patient table 46 and the gantry 12 to provide accessibility. Moving the floating cradle 50 through the door opening 212 enables a room length 216 of the scan room 210 to be further reduced (e.g., reduced to 3870 mm).

Figure 23:
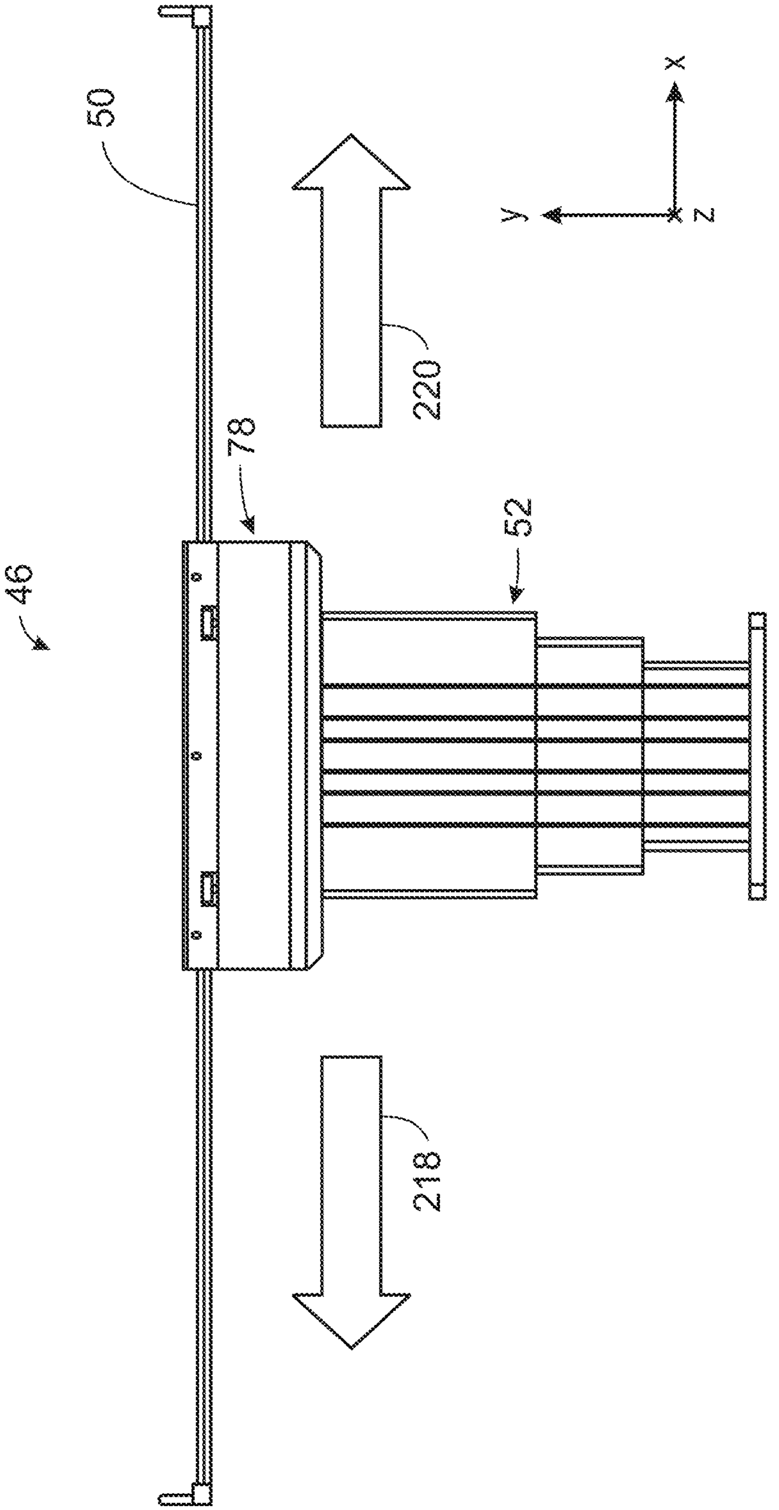
FIG. 23 is a side view of the patient table in FIG. 2, in accordance with aspects of the present disclosure.
Figure 24:
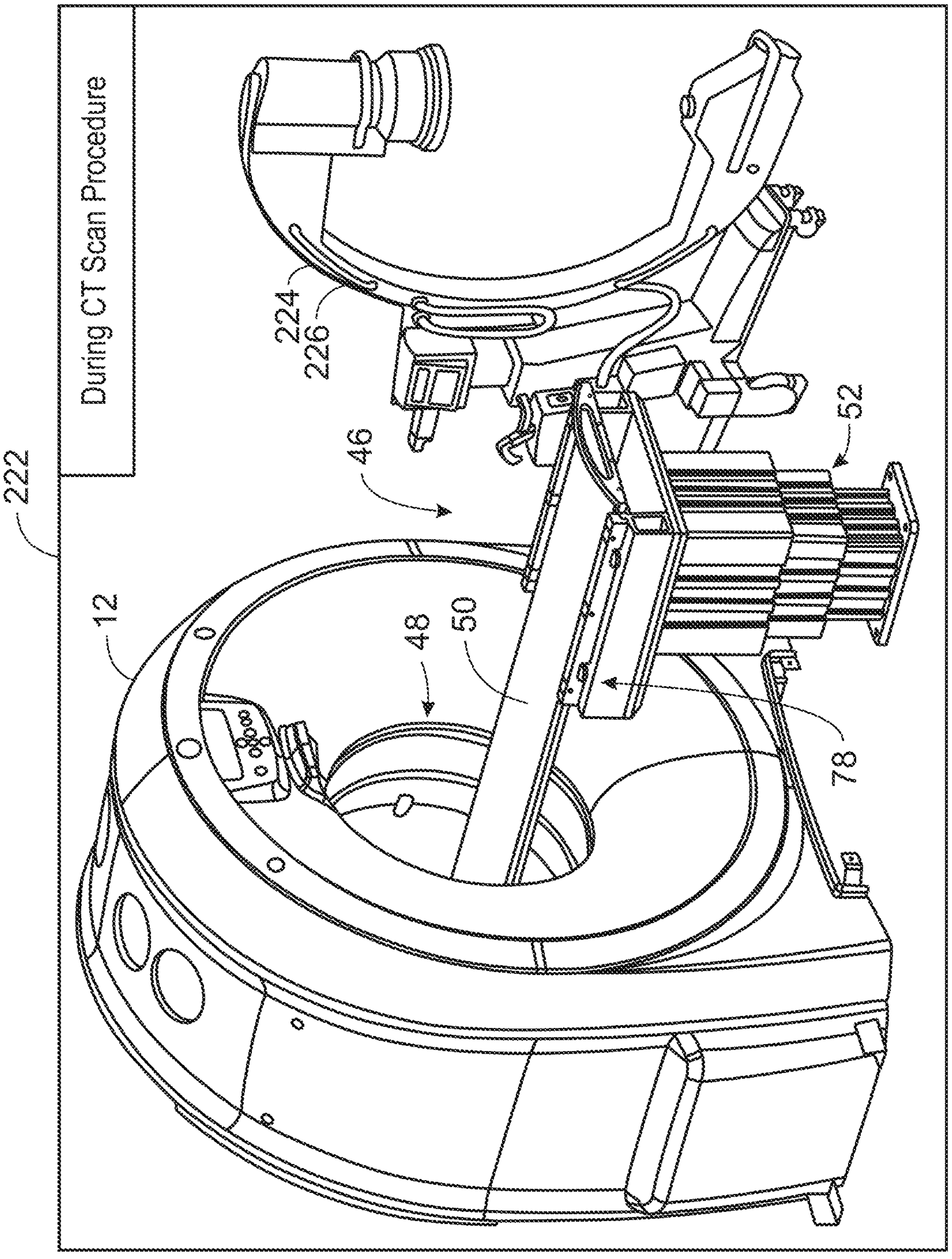
FIG. 24 is a schematic view of a scan room having a CT scanner and mobile C-arm imaging system with the patient table in FIG. 2 (e.g., during a CT scan room procedure), in accordance with aspects of the present disclosure.
Figure 25:
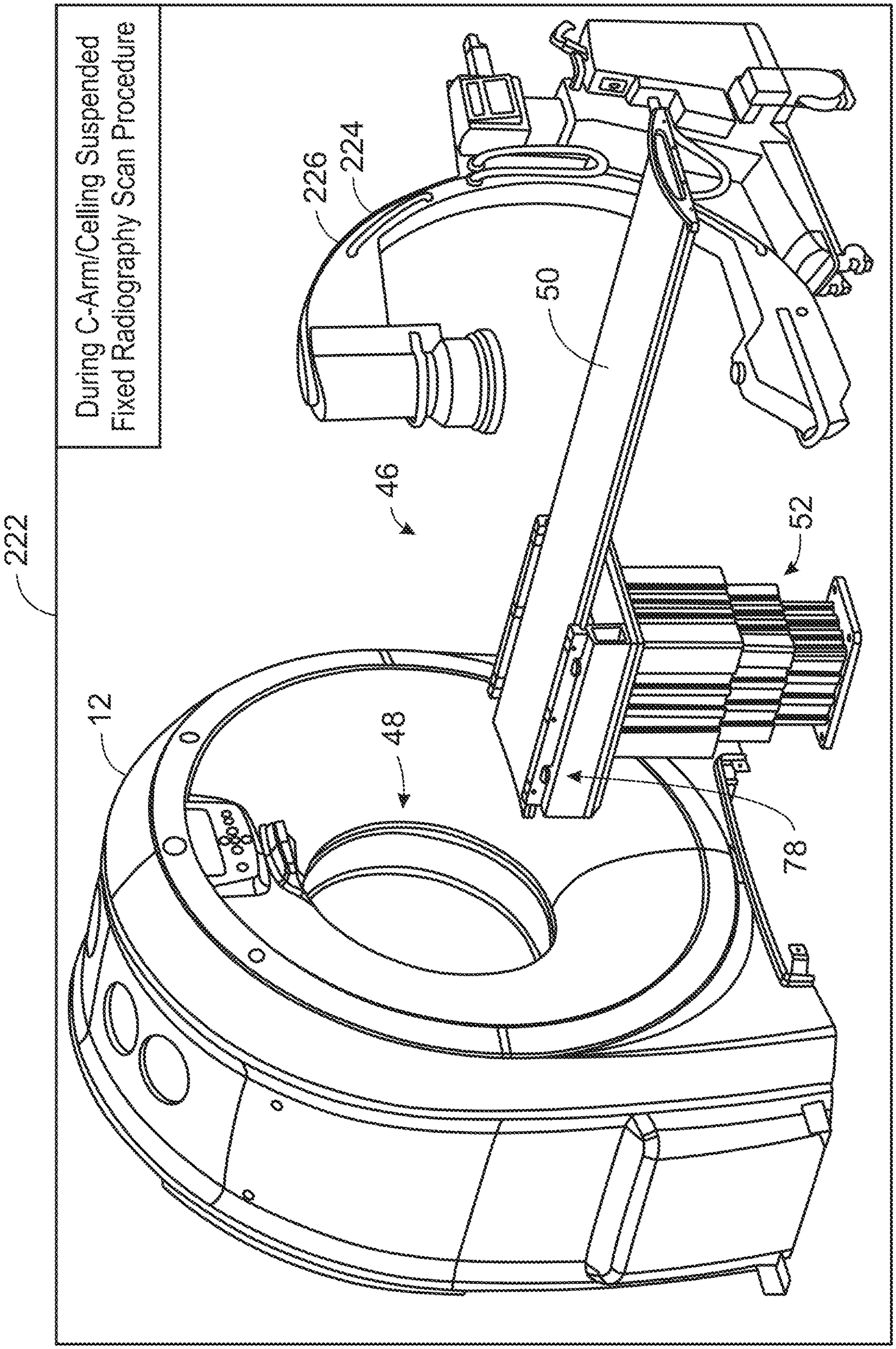
FIG. 25 is a schematic view of a scan room having a CT scanner and mobile C-arm imaging system with the patient table in FIG. 2 (during a fixed radiography scan procedure), in accordance with aspects of the present disclosure.

FIG. 23 is a side view of the patient table 46 in FIG. 2. The patient table 46 is as described in FIG. 2. Arrows 218 and 220 indicate the bi-directional movement of the floating cradle 50 relative to the fixed structure 78 along the x-direction. Due to the elimination of long metal beams structures (e.g., extruded beams) both sides of the patient table 46 are X-ray scannable utilizing the floating cradle 50. FIGS. 24 and 25 are schematic views of a scan room 222 having a CT scanner (e.g., gantry 12) and mobile C-arm imaging system 224 with the patient table 46 in FIG. 2. As depicted in FIG. 24, the patient table 46 is being utilized during a CT scan procedure with a portion of the floating cradle 50 disposed within the opening 48 of the gantry 12. As depicted in FIG. 25, the patient table 46 is being utilized during a fixed radiography scan procedure with the mobile C-arm imaging system 224. As depicted in FIG. 25, the floating cradle 50 is moved out of the opening 48 of the gantry 12 and is moved rearward from the fixed structure 78 and the base 52. A C-arm 226 of the C-arm imaging system 224 is disposed about the floating cradle 50. In certain embodiments, a ceiling suspended C-arm imaging system may similarly be utilized with the patient table 46. Due to the X-ray scan range availability on both sides of the patient table 46, as indicated in FIG. 23, a single patient table 46 can be used for multiple (e.g., separate and different) imaging devices in a common scan room 222 as depicted in FIGS. 24 and 25.

Figure 26:
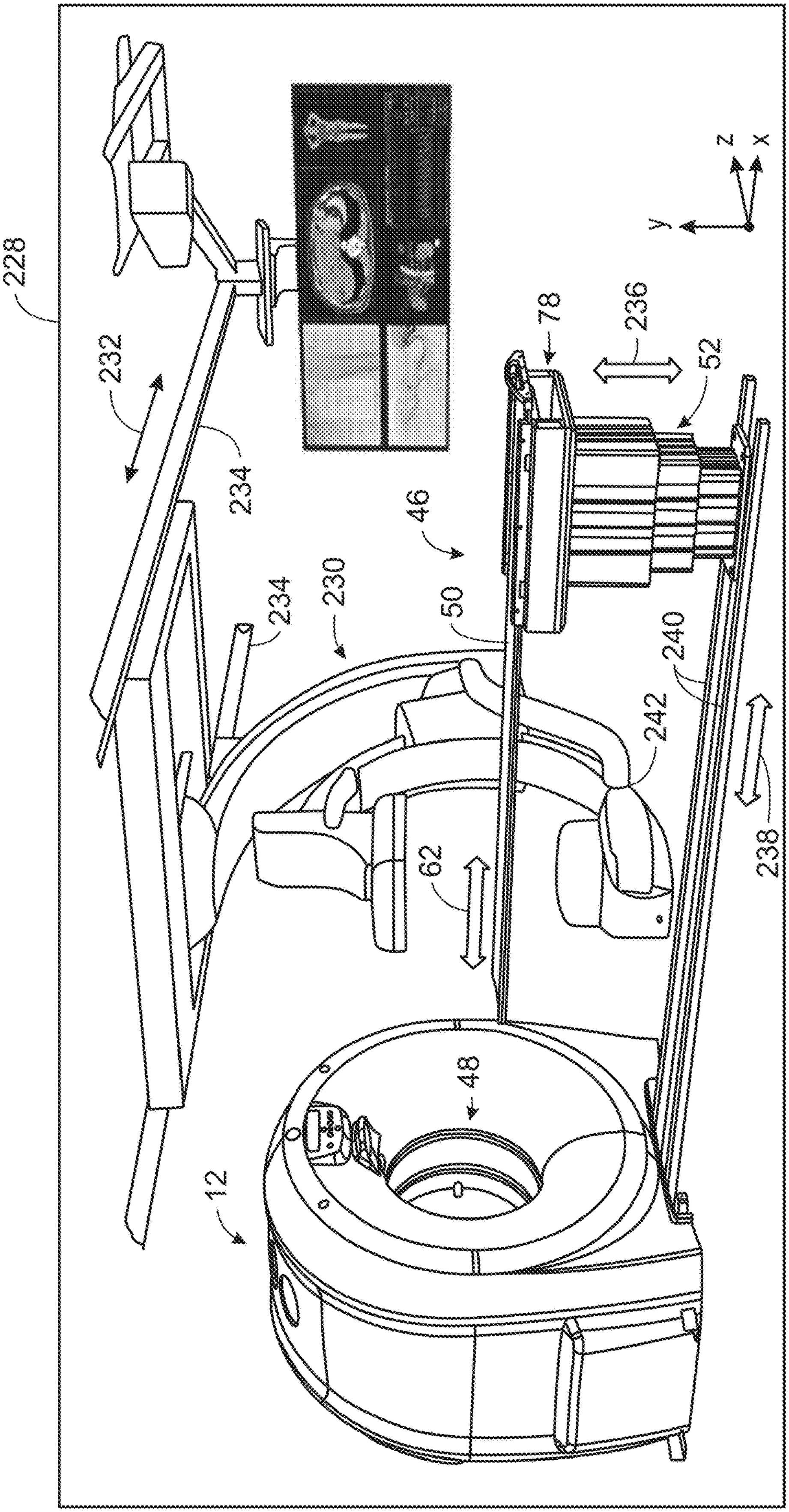
FIG. 26 is a schematic view of a scan room having a CT scanner and ceiling fixed C-arm imaging system with a patient table in FIG. 2, in accordance with aspects of the present disclosure.

FIG. 26 is a schematic view of a scan room 228 having a CT scanner (e.g., gantry 12) and a ceiling fixed C-arm imaging system 230 with the patient table 46 in FIG. 2. The patient table 46 is configured to be moved bi-directionally (as indicated by arrow 62) along the x-direction. The ceiling fixed C-arm imaging system 230 is configured to be moved bi-directionally (as indicated by arrow 232) along the z-direction via a pair of linear motion guide rails 234. The base 52 of the patient table 46 is configured to be moved bi-directionally (as indicated by arrow 236) in the y-direction. The patient table 46 is along configured to be moved bi-directionally (as indicated by arrow 238) in the x-direction by a pair of linear motion guide rails 240. The patient table 46 may be utilized during a CT scan procedure with the floating cradle 50 disposed within the opening 48 of the gantry 12. The patient table 46 may also be utilized during a fixed radiography scan procedure with the ceiling fixed C-arm imaging system 230 as depicted in FIG. 26. As depicted, a C-arm 242 of the ceiling fixed C-arm imaging system 230 is disposed about a portion of the floating cradle 50 (e.g., disposed between the gantry 12 and the fixed structure 78). As noted above, due to the X-ray scan range availability on both sides of the patient table 46, a single patient table 46 can be used for multiple (e.g., separate and different) imaging devices in a common scan room 228 as depicted in FIG. 26.

Technical effects of the disclosed embodiments include providing patient table having a floating cradle that reduces the room size requirement for the CT scanner. The technical effects of the disclosed embodiments also include making transportation, handling, and installation easier. The technical effects of the disclosed embodiments further include making serviceability easier due to the ease of gantry cover maneuvering which results in less downtime for the CT imaging system. The technical effects of the disclosed embodiments includes providing an enhanced platform for a patient table to be utilized with multiple imaging modalities. The technical effects of the disclosed embodiments yet further include reducing cost due to the elimination of using long beam structures. The technical effects of the disclosed embodiments even further include providing a low-cost solution for a multi-modality interventional/imaging environment within a common scan room. The technical effects of the disclosed embodiments yet further include providing a faster scan flow in this multi-modality interventional/imaging environment.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A patient table for a computed tomography (CT) imaging system, comprising:
- a base;
- a floating cradle configured to support a subject to be imaged and to move bi-directionally relative to the base;
- a fixed structure coupled to the base; and
- a plurality of rollers mounted to the fixed structure, wherein the plurality of rollers is configured to both guide and support the floating cradle, and the floating cradle is configured to guide itself when extended beyond the fixed structure, wherein the plurality of rollers comprises a first set of rollers disposed above the floating cradle and a second set of rollers disposed below the floating cradle, at least one roller of the second set of rollers is configured to support the floating cradle and at least one roller of the second set of rollers is configured to drive movement of the floating cradle bi-directionally relative to the base, and the second set of rollers comprises a friction drive roller configured to drive the movement of the floating cradle bi-directionally relative to the base and a pair of rollers flanking the friction drive roller and configured to support the floating cradle, and wherein the friction drive roller and the pair of rollers flanking the friction drive roller all contact a bottom surface of the floating cradle.

2. The patient table of claim 1, wherein the fixed structure comprises a pair of beams flanking a portion of the floating cradle, wherein the pair of beams extend in a direction parallel to a longitudinal axis of the floating cradle.

3. The patient table of claim 2, wherein a length of the floating cradle along the longitudinal axis is greater than a respective length of each beam of the pair of beams in the direction.

4. The patient table of claim 1, wherein the base is configured to move bi-directionally in a vertical direction.

5. The patient table of claim 1, wherein the first set of rollers is configured to retain the floating cradle on the fixed structure.

6. The patient table of claim 1, wherein the second set of rollers comprises a roller configured to support the floating cradle and a pair of friction drive rollers flanking the roller and configured to drive the movement of the floating cradle bi-directionally relative to the base.

7. The patient table of claim 1, wherein the plurality of rollers comprises a third set of rollers disposed on a first side and second side of the floating cradle, wherein both the first side and the second side extend between a top surface and the bottom surface of the floating cradle.

8. The patient table of claim 7, wherein at least one roller of the third set of rollers is configured to guide movement of the floating cradle bi-directionally relative to the base.

9. The patient table of claim 7, wherein at least one roller of the third set of rollers is configured to retain the floating cradle on the fixed structure.

10. The patient table of claim 7, wherein at least one roller of the third set of rollers is configured to drive movement of the floating cradle bi-directionally relative to the base.

11. The patient table of claim 10, wherein the third set of rollers comprises a first roller on disposed on the first side of the floating cradle and a second roller disposed on the second side of the floating cradle, and both the first roller and the second roller are configured to drive the movement of the floating cradle bi-directionally relative to the base.

12. The patient table of claim 1, further comprising a cable retractor, wherein the cable retractor comprises a first end structure coupled to the fixed structure, a second end structure coupled to a longitudinal end of the floating cradle, and a cord extending between the first end structure and the second end structure, wherein the cable retractor is configured to keep the longitudinal end of the floating cradle from extending beyond a fixed distance from the fixed structure, and wherein the cable retractor is configured to be adjusted to change or to set the fixed distance.

13. The patient table of claim 1, further comprising a sensor coupled to a longitudinal end of the floating cradle, wherein the sensor is configured to sense an object and to send a signal to stop movement of the floating cradle to avoid collision with the object.

14. The patient table of claim 1, wherein fixed structure comprises a first side and a second side opposite the first side, wherein the first side is configured to face a gantry of the CT imaging system, and wherein the floating cradle is configured to enable a scan of the subject on the floating cradle on at least one of the first side and the second side with an imaging system both separate from and different from the CT imaging system.

15. A computed tomography (CT) imaging system, comprising:
- a gantry coupled to imaging components configured to acquire imaging data of a subject; and
- a patient table comprising:
  - a base;
  - a floating cradle configured to support a subject to be imaged and to move bi-directionally relative to the base;
  - a fixed structure coupled to the base; and
  - a plurality of rollers mounted to the fixed structure, wherein the plurality of rollers is configured both to guide and to support the floating cradle, and the floating cradle is configured to guide itself when extended beyond the fixed structure, wherein the plurality of rollers comprises a first set of rollers disposed above the floating cradle and a second set of rollers disposed below the floating cradle, at least one roller of the second set of rollers is configured to support the floating cradle and at least one roller of the second set of rollers is configured to drive movement of the floating cradle bi-directionally relative to the base, and the second set of rollers comprises a friction drive roller configured to drive the movement of the floating cradle bi-directionally relative to the base and a pair of rollers flanking the friction drive roller and configured to support the floating cradle, and wherein the friction drive roller and the pair of rollers flanking the friction drive roller all contact a bottom surface of the floating cradle.

16. The CT imaging system of claim 15, wherein fixed structure comprises a first side and a second side opposite the first side, wherein the first side is configured to face the gantry of the CT imaging system, and wherein the floating cradle is configured to enable a scan of the subject on the floating cradle on at least one of the first side and the second side with an imaging system both separate from and different from the CT imaging system.

17. A patient table for an imaging system, comprising:

a base;

a floating cradle configured to support a subject to be imaged and to move bi-directionally relative to the base;

a fixed structure coupled to the base, wherein the fixed structure comprises a pair of beams flanking a portion of the floating cradle, wherein the pair of beams extend in a direction parallel to a longitudinal axis of the floating cradle, and wherein a first length of the floating cradle along the longitudinal axis is greater than a respective length of each beam of the pair of beams in the direction; and a cable retractor, wherein the cable retractor comprises a first end structure coupled to the fixed structure, a second end structure coupled to a longitudinal end of the floating cradle, and a cord extending between the first end structure and the second end structure, wherein the cable retractor is configured to keep the longitudinal end of the floating cradle from extending beyond a fixed distance from the fixed structure, and wherein the cable retractor is configured to be adjusted to change or to set the fixed distance.

* * * * *